United States Patent
Sato

(10) Patent No.: US 12,213,831 B2
(45) Date of Patent: Feb. 4, 2025

(54) ULTRASOUND DIAGNOSIS APPARATUS WITH ROW-COLUMN ADDRESSING

(71) Applicant: CANON MEDICAL SYSTEMS CORPORATION, Tochigi (JP)

(72) Inventor: Takeshi Sato, Nasushiobara (JP)

(73) Assignee: CANON MEDICAL SYSTEMS CORPORATION, Tochigi (JP)

(*) Notice: Subject to any disclaimer, the term of this patent is extended or adjusted under 35 U.S.C. 154(b) by 178 days.

(21) Appl. No.: 17/740,853

(22) Filed: May 10, 2022

(65) Prior Publication Data

US 2022/0361843 A1    Nov. 17, 2022

(30) Foreign Application Priority Data

May 11, 2021    (JP) ................. 2021-080439

(51) Int. Cl.
| | |
|---|---|
| *A61B 8/14* | (2006.01) |
| *G01S 7/52* | (2006.01) |
| *G01S 15/89* | (2006.01) |
| *G10K 11/34* | (2006.01) |

(52) U.S. Cl.
CPC ............. *A61B 8/14* (2013.01); *G01S 7/5208* (2013.01); *G01S 15/8927* (2013.01); *G10K 11/346* (2013.01)

(58) Field of Classification Search
CPC ............. G01S 15/8927; G01S 15/8913; G01S 15/8925
See application file for complete search history.

(56) References Cited

U.S. PATENT DOCUMENTS

| | | | | |
|---|---|---|---|---|
| 5,797,845 A * | 8/1998 | Barabash | ............. | A61B 8/4281 600/443 |
| 5,860,926 A * | 1/1999 | Barabash | ............. | G01S 15/8925 600/443 |
| 6,352,510 B1 * | 3/2002 | Barabash | ............. | G01S 15/8925 600/443 |
| 9,855,022 B2 | 1/2018 | Christiansen et al. | | |

(Continued)

OTHER PUBLICATIONS

Japanese Office Action dated Oct. 2, 2024, issued in Japanese Patent Application No. 2021-080439 (with English translation from Global Dossier).

*Primary Examiner* — Joel Lamprecht
*Assistant Examiner* — Nyrobi Celestine
(74) *Attorney, Agent, or Firm* — Oblon, McClelland, Maier & Neustadt, L.L.P.

(57) ABSTRACT

An ultrasound diagnosis apparatus according to an embodiment includes an ultrasound probe and processing circuitry. The ultrasound probe includes a plurality of transducer elements arranged two-dimensionally and includes a plurality of transducer element groups of a Row-Column Addressing type in which, when ultrasound transmission is to be performed, a plurality of first transducer elements arranged in the direction of one of two axes intersecting each other are connected in common to one another and in which, when ultrasound reception is to be performed, a plurality of second transducer elements arranged in the direction of the other of the two axes are connected in common to one another. A plurality of sets that are each made up of the two axes and correspond to the plurality of transducer element groups of the Row-Column Addressing type are mutually different.

10 Claims, 19 Drawing Sheets

(56) References Cited

U.S. PATENT DOCUMENTS

| | | |
|---|---|---|
| 2003/0055308 A1* | 3/2003 | Friemel ................... A61B 8/14 |
| | | 600/15 |
| 2008/0146930 A1* | 6/2008 | Takeuchi ............. G10K 11/341 |
| | | 600/447 |
| 2011/0028846 A1* | 2/2011 | Tsao ..................... G10K 11/345 |
| | | 600/459 |
| 2015/0087991 A1 | 3/2015 | Chen et al. |
| 2015/0374335 A1* | 12/2015 | Brown ................. A61B 8/4488 |
| | | 367/87 |
| 2018/0271492 A1* | 9/2018 | Jeon ..................... A61B 8/4488 |
| 2018/0348624 A1* | 12/2018 | Jensen ............... G10K 11/346 |
| 2020/0064468 A1 | 2/2020 | Holbek et al. |

\* cited by examiner

QUANTITY OF ELECTRONIC CIRCUITS: $N^2$

QUANTITY OF ELECTRONIC CIRCUITS: N

QUANTITY OF ELECTRONIC CIRCUITS: N

ULTRASOUND DIAGNOSIS APPARATUS WITH ROW-COLUMN ADDRESSING

CROSS-REFERENCE TO RELATED APPLICATIONS

This application is based upon and claims the benefit of priority from Japanese Patent Application No. 2021-080439, filed on May 11, 2021; the entire contents of which are incorporated herein by reference.

FIELD

Embodiments described herein relate generally to an ultrasound diagnosis apparatus.

BACKGROUND

Some ultrasound diagnosis apparatuses are configured to three-dimensionally scan a patient's body electronically. Examples of methods used by an ultrasound diagnosis apparatus for three-dimensionally scanning a patient's body electronically include the following method. FIG. 1A is a diagram illustrating an exemplary configuration of a conventional ultrasound diagnosis apparatus 200. As illustrated in FIG. 1A, the conventional ultrasound diagnosis apparatus 200 includes an ultrasound probe 201 and an apparatus main body 202.

The ultrasound probe 201 includes a plurality of transducer elements 203 arranged two-dimensionally and electronic circuits 204. The plurality of transducer elements 203 arranged two-dimensionally may also be referred to as two-dimensional array transducer elements. FIG. 1B is a diagram illustrating an exemplary configuration of the conventional ultrasound probe 201. As illustrated in FIG. 1B, in a two-dimensional coordinate system having an x-axis and a y-axis, while each of the transducer element columns includes N transducer elements 203 arranged along the x-axis direction (where N is a natural number), as many transducer element columns as N are arranged along the y-axis direction. In other words, in the example in FIG. 1B, the ultrasound probe 201 includes the transducer elements 203 of which the quantity is equal to $N^2$ (N×N). As illustrated in FIG. 1A, each of the $N^2$ transducer elements 203 is organized so as to belong to one of a plurality of groups called subarrays each including M transducer elements 203 (where M is a natural number smaller than N).

The electronic circuits 204 include a plurality of blocks 205. Each of the blocks 205 is provided in correspondence with a different one of the subarrays. In other words, each of the blocks 205 is provided for a different one of the subarrays. Each of the blocks 205 is configured to cause the M transducer elements 203 included in the corresponding subarray to perform ultrasound transmission and reception.

Each of the blocks 205 includes one transmission beam former 205a, M pulsers 205b, M Transmission/Reception (T/R) switches 205c, M Low Noise Amplifiers (LNAs) 205d, M Variable Gain Amplifiers (VGAs) 205e, and one reception subarray beam former 205f. Among these, a transmission system is formed by the transmission beam former 205a and the pulsers 205b, whereas a reception system is formed by the LNAs 205d, the VGAs 205e, and the reception subarray beam former 205f.

In correspondence with each of the transducer elements 203, one pulser 205b, one transmission/reception switch 205c, one LNA 205d, and one VGA 205e are provided. Further, in correspondence with each of the subarrays, one reception subarray beam former 205f is provided.

An operation in each of the blocks 205 included in the ultrasound probe 201 will be explained. When ultrasound transmission is to be performed, the transmission beam former 205a is configured to cause each of the plurality of (M) transducer elements 203 to transmit a delay-controlled ultrasound wave, via the corresponding pulser 205b. In other words, each of the pulsers 205b is configured to supply a delay-controlled drive signal to the corresponding transducer element 203. Each of the transmission/reception switches 205c is configured to separate the reception system and the transmission system from each other so as to prevent the transmission system from applying voltage to the reception system at the time of the ultrasound transmission. When ultrasound reception is to be performed, the transmission/reception switches 205c are configured to separate reception signals transmitted from the individual transducer elements 203 from the transmission system. Further, the LNAs 205d are configured to amplify the reception signals. Further, the VGAs 205e are configured to adjust gain of the amplified reception signals in accordance with depths. Further, the reception subarray beam former 205f is configured to apply a reception delay to the M gain-adjusted reception signals and to add up the M reception signals to which the reception delay was applied. Further, the reception subarray beam former 205f is configured to output a reception signal resulting from the addition, to the apparatus main body 202. In other words, the reception subarray beam formers 205f are configured to apply the reception delay to the reception signals in units of groups called the subarrays, to add up the signals, and to output the reception signals resulting from the addition. The beam forming process (a reception beam forming process) for each of the subarrays described above may be referred to as a subarray beam forming process. In this manner, the ultrasound probe 201 is configured to output as many reception signals as the quantity of the subarrays, to the apparatus main body 202.

The apparatus main body 202 includes a reception beam former 206. The reception beam former 206 is configured to apply a reception delay to the plurality of reception signals (as many reception signals as the quantity of the subarrays) output from the ultrasound probe 201 and to add up the reception signals to which the reception delay was applied. Further, the apparatus main body 202 is configured to generate ultrasound image data by using a signal resulting from the addition.

Further, for the (N×N) two-dimensional array transducer elements (the $N^2$ transducer elements arranged in the formation of N rows in the row direction by N columns in the column direction) as illustrated in FIG. 1B, as many pulsers 205b as $N^2$, as many LNAs 205d as $N^2$, and as many VGAs 205e as $N^2$ are used, as illustrated in FIG. 1A. This configuration will hereinafter be referred to as "2DA". An electronic circuit including the $N^2$ pulsers 205b, the $N^2$ LNAs 205d, and the $N^2$ VGAs 205e is provided inside the ultrasound probe 201, for example, as illustrated in FIG. 1A.

In this situation, as the value of N increases, the quantity of the electronic circuits dramatically increases. For this reason, problems arise from the viewpoint of the installation area, heat generation, and the like. For example, when the value of N is 128, it is necessary to have 16,384 pulsers 205b, 16,384 LNAs 205d, and 16,384 VGAs 205e. When a set made up of one pulser 205b, one LNA 205d, and one VGA 205e is regarded as one electronic circuit, it is necessary to have 16,384 electronic circuits. From the viewpoint of the installation area, heat generation, and the like, it would be difficult to install the electronic circuits in such a large quantity on the inside of the ultrasound probe 201.

According to the conventional technique of the subarray beam forming described above, when the reception beam forming process is performed inside the ultrasound probe 201 for each of the M transducer elements 203, the quantity of the cables used for connecting the ultrasound probe 201 to the apparatus main body 202 is (1/M) times as large as the quantity of the cables used when the subarray beam forming is not performed. Accordingly, it is possible to reduce the quantity of the cables by performing the subarray beam forming processes. However, the quantity of the electronic circuits such as the pulsers 205*b*, the LNAs 205*d*, and the VGAs 205*e* are not reduced.

In relation to the above, as a conventional method for reducing the quantity of the electronic circuits, known techniques include a conventional technique called Row-Column Addressing (RCA), which is disclosed in a patent document (U.S. Pat. No. 9,855,022) and the like.

An example of the conventional technique called RCA will be explained. FIGS. 2A and 2B are drawings for explaining the example of the RCA scheme. FIG. 3 is a diagram illustrating an exemplary configuration of a conventional ultrasound diagnosis apparatus 300 having a structure of the example of the RCA scheme explained with reference to FIGS. 2A and 2B. As illustrated in FIG. 3, the ultrasound diagnosis apparatus 300 includes an ultrasound probe 301 and an apparatus main body 302.

The ultrasound probe 301 includes N×N two-dimensional array transducer elements. In other words, as illustrated in FIGS. 2A and 2B, the ultrasound probe 301 includes, as a transducer element group (a transducer element array) having an RCA structure, $N^2$ transducer elements 303 that are arranged in the formation of N rows in the row direction (an x-axis direction) by N columns in the column direction (a y-axis direction). In this manner, the ultrasound diagnosis apparatus 300 illustrated in FIG. 3 includes the transducer element group having the RCA structure.

The apparatus main body 302 includes as many pulsers 304 as N, a transmission beam former 305, as many LNAs 306 as N, as many VGAs 307 as N, and a reception beam former 308.

An operation performed by the ultrasound diagnosis apparatus 300 will be explained. When the ultrasound diagnosis apparatus 300 is to perform ultrasound transmission, as illustrated in FIG. 2A, one of the two surfaces (e.g., the front surface) of each of the N transducer elements 303 arranged in the column direction (the y-axis direction) are connected in common to one another. In other words, in the ultrasound diagnosis apparatus 300, the N transducer elements 303 arranged in the column direction (the y-axis direction) are connected in common to one another. As a result, while each of the transducer element groups 303*a* includes the N transducer elements 303 that are connected in series and arranged in the column direction, as many transducer element groups 303*a* as N are arranged in the row direction (the x-axis direction).

As illustrated in FIG. 3, one pulser 304 is provided for each of the transducer element groups 303*a*. Because the quantity of the transducer element groups 303*a* is N, the apparatus main body 302 includes as many pulsers 304 as N. Accordingly, when each of the pulsers 304 is regarded as one electronic circuit, the apparatus main body 302 needs N electronic circuits when the ultrasound diagnosis apparatus 300 performs ultrasound transmission.

Further, via the pulsers 304, the transmission beam former 305 is configured to cause an ultrasound wave to which a transmission delay is applied in the row direction to be transmitted from the other surfaces (e.g., the rear surfaces) of the N transducer elements 303 included in the transducer element groups 303*a*. The transmission beam former 305 is configured to perform this process for each of the transducer element groups 303*a*.

Subsequently, when the ultrasound diagnosis apparatus 300 is to perform ultrasound reception, as illustrated in FIG. 2B, the other (e.g., the rear surface) of the two surfaces of each of the N transducer elements 303 arranged in the row direction (the x-axis direction) are connected in common to one another. In other words, in the ultrasound diagnosis apparatus 300, the N transducer elements 303 arranged in the row direction (the x-axis direction) are connected in common to one another. As a result, while each of the transducer element groups 303*b* includes the N transducer elements 303 that are connected in series and arranged in the row direction, as many transducer element groups 303*b* as N are arranged in the column direction (the y-axis direction).

As illustrated in FIG. 3, one LNA 306 and one VGA 307 are provided for each of the transducer element groups 303*b*. Because the quantity of the transducer element groups 303*b* is N, the apparatus main body 302 includes as many LNAs 306 as N and as many VGAs 307 as N.

Each of the LNAs 306 is configured to amplify a reception signal output from the corresponding transducer element group 303*b*. In this situation, the reception signal output from each of the transducer element groups 303*b* is a reception signal obtained by adding up (combining) M reception signals output from the M transducer elements 303 included in the transducer element group 303*b*. Further, each of the VGAs 307 is configured to adjust gain of the amplified reception signal in accordance with depth. Further, an Analog to Digital (A/D) converter is configured to convert the reception signal, which is the gain-adjusted signal in an analog format (an analog signal), into a signal in a digital format (a digital signal). After that, the reception beam former 308 is configured to apply a reception delay to the N gain-adjusted reception signals (the digital signals) and to add up the N reception signals to which the reception delay was applied. Further, the apparatus main body 302 is configured to generate ultrasound image data by using the reception signal resulting from the addition.

As illustrated in FIG. 3, one LNA 306 and one VGA 307 are provided for each of the transducer element groups 303*b*. Because the quantity of the transducer element groups 303*b* is N, the apparatus main body 302 includes as many LNAs 306 as N and as many VGAs 307 as N. Accordingly, when a set made up of one LNA 306 and one VGA 307 is regarded as one electronic circuit, the apparatus main body 302 needs N electronic circuits when the ultrasound diagnosis apparatus 300 performs ultrasound reception. Consequently, when the ultrasound diagnosis apparatus 300 performs ultrasound transmission and reception, the apparatus main body 302 needs 2N electronic circuits. For example, when the value of N is 128, the ultrasound diagnosis apparatus 200 needs 16,384 electronic circuits as explained above. In contrast, the ultrasound diagnosis apparatus 300 needs only 256 (2×128) electronic circuits. In this situation, the quantity of the electronic circuits needed by the ultrasound diagnosis apparatus 300 is $\frac{1}{64}$ times as large as the quantity of the electronic circuits needed by the ultrasound diagnosis apparatus 200. Accordingly, the ultrasound diagnosis apparatus 300 is able to significantly reduce the quantity of the electronic circuits that are needed.

Further, because the reception system and the transmission system are separated from each other to begin with, it is not necessary to provide a transmission/reception switch for separating the reception system from the transmission system. In this aspect also, the ultrasound diagnosis apparatus 300 is able to reduce the quantity of the electronic circuits, compared to the ultrasound diagnosis apparatus 200.

However, the image quality of an ultrasound image based on the ultrasound image data generated by the ultrasound diagnosis apparatus 300 is significantly lower than the image quality of an ultrasound image based on the ultrasound image data generated by the ultrasound diagnosis apparatus 200.

FIG. 4A is a contour line chart at 6-dB intervals expressing a Point Spread Function (PSF) of the ultrasound diagnosis apparatus 200 based on the 2DA scheme, as viewed from a z-axis direction. In the situation depicted in FIG. 4A, reception apodization and transmission apodization are not implemented. In this situation, the reception apodization is a technique by which, for example, reception signals that are from mutually the same sampling points and are received by a plurality of transducer elements structuring a reception aperture of an ultrasound probe are weighted by using an apodization function (an aperture function), before performing a phased addition process. The apodization function is a mathematical function set with a weight for each of different positions of the transducer elements. Further, the transmission apodization is a technique by which, for example, the amplitude of an ultrasound wave transmitted by a plurality of transducer elements structuring a transmission aperture of an ultrasound probe is varied for each of different positions of the transducer elements.

FIGS. 4B and 4C are each a contour line chart at 6-dB intervals expressing a PSF of the ultrasound diagnosis apparatus 300 including the transducer element groups having the RCA structure, as viewed from the z-axis direction. In the example in FIG. 4B, reception apodization and transmission apodization are not implemented. In contrast, in the example in FIG. 4C, reception apodization and transmission apodization are implemented.

FIG. 5A expresses the situation in FIG. 4A by using an image 210 depicting the range from the peak to −40 dB. FIG. 5B expresses the situation in FIG. 4B by using an image 310 depicting the range from the peak to −40 dB. FIG. 5C expresses the situation in FIG. 4C by using an image 311 depicting the range from the peak to −40 dB.

As the image 210 is compared with the image 310, it is observed that, with the ultrasound diagnosis apparatus 300 not implementing the reception apodization and the transmission apodization, the main lobe has slightly spread, and the spatial resolution is lower, compared to the example with the ultrasound diagnosis apparatus 200. Further, as the image 210 is compared with the image 310, it is observed that, with the ultrasound diagnosis apparatus 300 not implementing the reception apodization and the transmission apodization, there are larger side lobes along the x-axis and the y-axis compared to the example with the ultrasound diagnosis apparatus 200, which means that artifacts occur more easily.

As the image 210 is compared with the image 310 and the image 311, it is observed that, with the ultrasound diagnosis apparatus 300 implementing the reception apodization and the transmission apodization, the main lobe has significantly spread, and the spatial resolution is significantly lower, compared to the examples with the ultrasound diagnosis apparatus 200 and the ultrasound diagnosis apparatus 300 not implementing the reception apodization and the transmission apodization. Further, as the image 210 is compared with the image 310 and the image 311, with the ultrasound diagnosis apparatus 300 implementing the reception apodization and the transmission apodization, the side lobes along the x-axis and the y-axis are smaller than those in the example with the ultrasound diagnosis apparatus 300 not implementing the reception apodization and the transmission apodization, but the side lobes along the x-axis and the y-axis are larger compared to those in the example with the ultrasound diagnosis apparatus 200. Accordingly, it is understood that, with the ultrasound diagnosis apparatus 300 implementing the reception apodization and the transmission apodization, artifacts occur more easily than in the example with the ultrasound diagnosis apparatus 200.

As explained above, in comparison to the ultrasound diagnosis apparatus 200 based on the 2DA scheme, the ultrasound diagnosis apparatus 300 including the transducer element groups having the RCA structure has an advantage where the quantity of the necessary electronic circuits is reduced, but has a problem where the image quality is not satisfactory.

DETAILED DESCRIPTION

One of the problems to be solved by the embodiments described in the present disclosure is to improve the image quality of ultrasound images obtained by using transducer element groups having the RCA structure. However, problems to be solved by the embodiments described in the present disclosure are not limited to the problem described above. It is also possible to consider problems corresponding to advantageous effects achieved by the configurations in the embodiments described below, as other problems.

An ultrasound diagnosis apparatus according to an embodiment includes an ultrasound probe and processing circuitry. The ultrasound probe includes a plurality of transducer elements arranged two-dimensionally and includes a plurality of transducer element groups of a Row-Column Addressing type in which, when ultrasound transmission is to be performed, a plurality of first transducer elements arranged in the direction of one of two axes intersecting each other are connected in common to one another and in which, when ultrasound reception is to be performed, a plurality of second transducer elements arranged in the direction of the other of the two axes are connected in common to one another. With respect to each of the plurality of transducer element groups, the processing circuitry is configured to perform a beam forming process on a plurality of reception signals output from the plurality of second transducer elements and to generate ultrasound image data on the basis of a signal obtained from the beam forming processes. The processing circuitry is configured to cause a display device to display an ultrasound image based on the ultrasound image data. A plurality of sets that are each made up of the two axes and correspond to the plurality of transducer element groups of the Row-Column Addressing type are mutually different.

At first, before explaining ultrasound diagnosis apparatuses according to embodiments, an example will be explained in which an ultrasound diagnosis apparatus including transducer element groups having the RCA structure is configured to generate ultrasound image data while rotating the transducer element groups having the RCA structure.

Figure 6A:
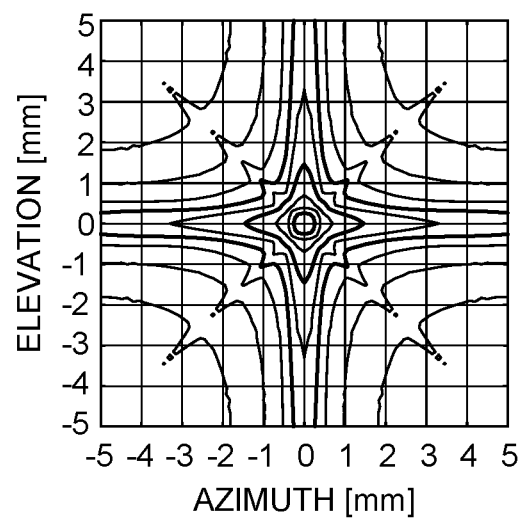
FIG. 6A is a contour line chart at 6-dB intervals expressing a PSF of an ultrasound diagnosis apparatus including transducer element groups having an RCA structure, as viewed from the z-axis direction.

FIG. 6A is a contour line chart at 6-dB intervals expressing a PSF of the ultrasound diagnosis apparatus 300 including the transducer element groups having the RCA structure, as viewed from the z-axis direction.

Figure 6B:
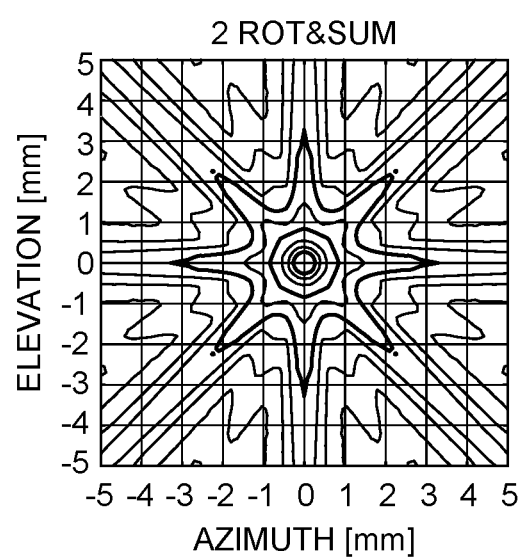
FIG. 6B is a contour line chart at 6-dB intervals expressing a PSF viewed from the z-axis direction, regarding the ultrasound diagnosis apparatus configured to obtain a reception signal to be supplied to signal processing circuitry, by adding up reception signals obtained through beam forming processes performed on reception signals obtained at various angles while rotating the transducer element groups having the RCA structure at 45-degree intervals in the range equal to or larger than 0° and smaller than 90°.

FIG. 6B is a contour line chart at 6-dB intervals expressing a PSF viewed from the z-axis direction, regarding the ultrasound diagnosis apparatus 300 configured to obtain a reception signal to be supplied to signal processing circuitry, by adding together: a reception signal obtained through a beam forming process performed on a reception signal obtained when the angle of the transducer element groups having the RCA structure is 0° being a predetermined reference angle; and another reception signal obtained through a beam forming process performed on a reception signal obtained when the angle of the transducer element groups having the RCA structure is 45° as a result of the transducer element groups having the RCA structure being rotated by 45° from the predetermined reference angle. In other words, FIG. 6B is a contour line chart at 6-dB intervals expressing the PSF viewed from the z-axis direction, regarding the ultrasound diagnosis apparatus 300 configured to obtain the reception signal to be supplied to the signal processing circuitry, by adding up the reception signals obtained through the beam forming processes performed on the reception signals obtained at the various angles while rotating the transducer element groups having the RCA structure at 45-degree intervals in the range equal to or larger than 0° and smaller than 90°.

Figure 6C:
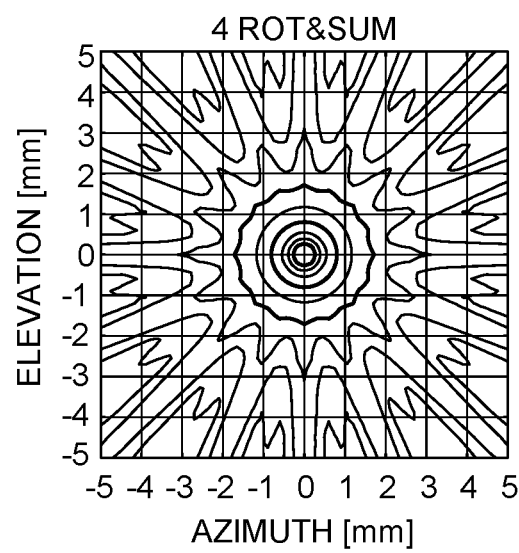
FIG. 6C is a contour line chart at 6-dB intervals expressing a PSF viewed from the z-axis direction, regarding the ultrasound diagnosis apparatus configured to obtain a reception signal to be supplied to signal processing circuitry, by adding up reception signals obtained through beam forming processes performed on reception signals obtained at various angles while rotating the transducer element groups having the RCA structure at 22.5-degree intervals in the range equal to or larger than 0° and smaller than 90°.

FIG. 6C is a contour line chart at 6-dB intervals expressing a PSF viewed from the z-axis direction, regarding the ultrasound diagnosis apparatus 300 configured to obtain a reception signal to be supplied to signal processing circuitry, by adding together: a reception signal obtained through a beam forming process performed on a reception signal obtained when the angle of the transducer element groups having the RCA structure is 0° being the predetermined reference angle; another reception signal obtained through a beam forming process performed on a reception signal obtained when the angle of the transducer element groups having the RCA structure is 22.5° as a result of the transducer element groups having the RCA structure being rotated by 22.5° from the predetermined reference angle; yet another reception signal obtained through a beam forming process performed on a reception signal obtained when the angle of the transducer element groups having the RCA structure is 45° as a result of the transducer element groups having the RCA structure being rotated by 45° from the predetermined reference angle; and yet another reception signal obtained through a beam forming process performed on a reception signal obtained when the angle of the transducer element groups having the RCA structure is 67.5° as a result of the transducer element groups having the RCA structure being rotated by 67.5° from the predetermined reference angle. In other words, FIG. 6C is a contour line chart at 6-dB intervals expressing the PSF viewed from the z-axis direction, regarding the ultrasound diagnosis apparatus 300 configured to obtain the reception signal to be supplied to the signal processing circuitry, by adding up the reception signals obtained through the beam forming processes performed on the reception signals obtained at the various angles while rotating the transducer element groups having the RCA structure at 22.5-degree intervals in the range equal to or larger than 0° and smaller than 90°.

Figure 6D:
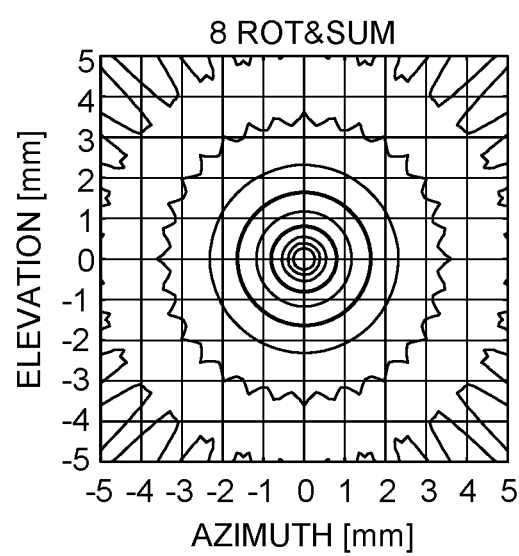
FIG. 6D is a contour line chart at 6-dB intervals expressing a PSF viewed from the z-axis direction, regarding the ultrasound diagnosis apparatus configured to obtain a reception signal to be supplied to signal processing circuitry, by adding up reception signals obtained through beam forming processes performed on reception signals obtained at various angles while rotating the transducer element groups having the RCA structure at 11.25-degree intervals in the range equal to or larger than 0° and smaller than 90°.

FIG. 6D is a contour line chart at 6-dB intervals expressing a PSF viewed from the z-axis direction, regarding the ultrasound diagnosis apparatus 300 configured to obtain a reception signal to be supplied to signal processing circuitry, by adding up reception signals obtained through beam forming processes performed on reception signals obtained at various angles while rotating the transducer element groups having the RCA structure at 11.25-degree intervals in the range equal to or larger than 0° and smaller than 90°.

In the examples illustrated in FIGS. 6A to 6D, the reception apodization and the transmission apodization are not implemented.

Figure 7A:
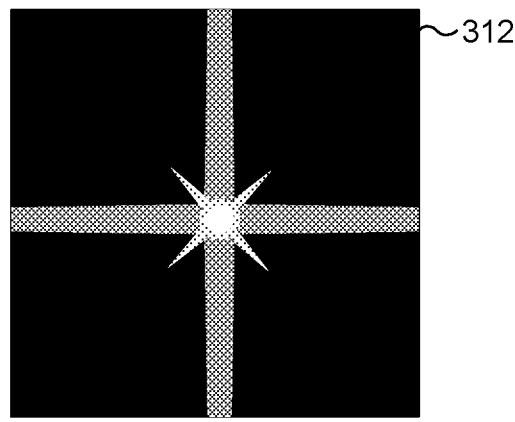
FIG. 7A is a drawing expressing the situation in FIG. 6A by using an image depicting the range from the peak to −40 dB.
Figure 7B:
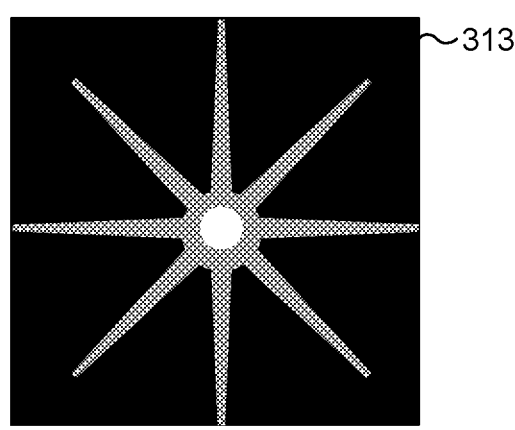
FIG. 7B is a drawing expressing the situation in FIG. 6B by using an image depicting the range from the peak to −40 dB.
Figure 7C:
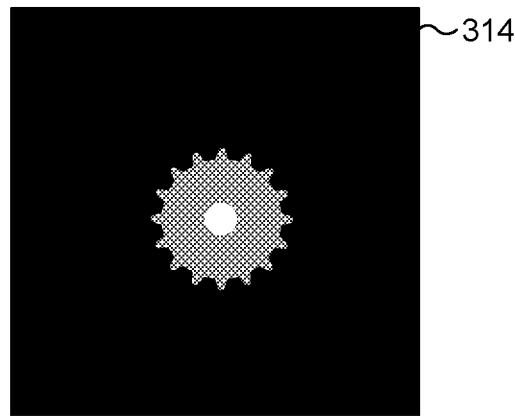
FIG. 7C is a drawing expressing the situation in FIG. 6C by using an image depicting the range from the peak to −40 dB.
Figure 7D:
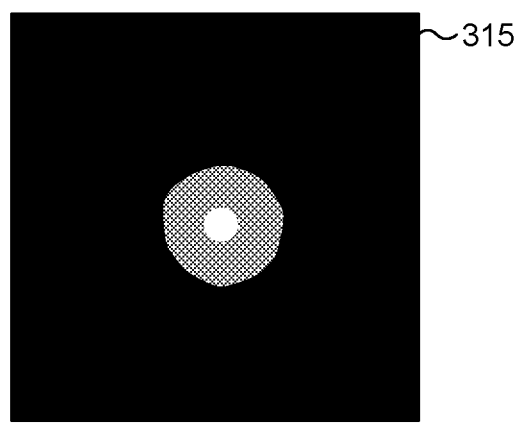
FIG. 7D is a drawing expressing the situation in FIG. 6D by using an image depicting the range from the peak to −40 dB.

FIG. 7A is a drawing expressing the situation in FIG. 6A by using an image 312 depicting the range from the peak to −40 dB. FIG. 7B is a drawing expressing the situation in FIG. 6B by using an image 313 depicting the range from the peak to −40 dB. FIG. 7C is a drawing expressing the situation in FIG. 6C by using an image 314 depicting the range from the peak to −40 dB. FIG. 7D is a drawing expressing the situation in FIG. 6D by using an image 315 depicting the range from the peak to −40 dB.

Figure 4A:
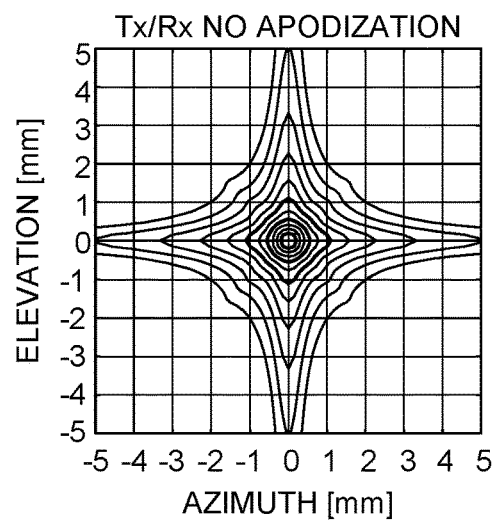
FIG. 4A is a contour line chart at 6-dB intervals expressing a Point Spread Function (PSF) of the ultrasound diagnosis apparatus based on the 2DA scheme, as viewed from a z-axis direction.
Figure 4B:
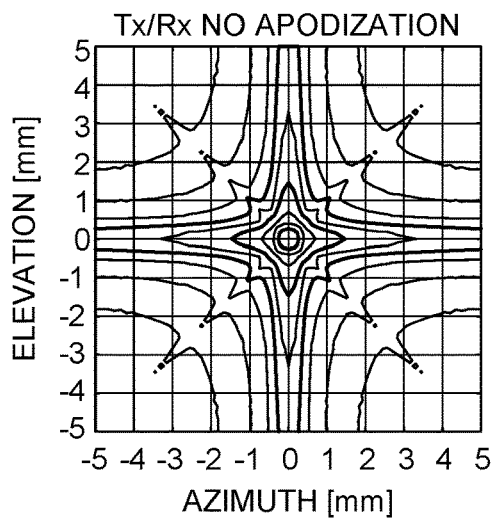
FIG. 4B is a contour line chart at 6-dB intervals expressing a PSF of the ultrasound diagnosis apparatus implementing RCA, as viewed from the z-axis direction.
Figure 4C:
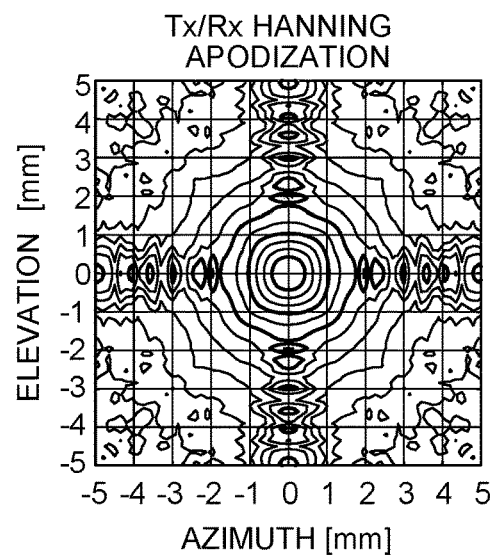
FIG. 4C is another contour line chart at 6-dB intervals expressing the PSF of the ultrasound diagnosis apparatus implementing RCA, as viewed from the z-axis direction.

In the order of the images 312, 313, 314, and 315, the sidelobes in the four cross-like directions gradually decrease. More specifically, in the image 312, the side lobes in the four cross-like directions are clearly present, but in the image 315, these side lobes have almost disappeared. In the examples in FIGS. 4C and 5C presented earlier, the side lobes are decreased by implementing the reception apodization and the transmission apodization. In contrast, from the images 313 to 315, it is observed that it is possible to decrease or eliminate the side lobes without applying these apodization processes. Because no apodization is applied, it is possible to decrease the side lobes, while preventing the main lobe from increasing, i.e., while preventing the spatial resolution from becoming lower.

However, rotating the transducer element groups having the RCA structure is not realistic. For example, it is sometimes difficult to rotate the transducer elements having the RCA structure when the transducer element groups having the RCA structure are in contact with an examined subject. Further, while the transducer element groups having the RCA structure are rotating, the examined subject may move. To cope with these situations, the ultrasound diagnosis apparatuses according to the embodiments described below are configured so as to be able to decrease the side lobes, while preventing the spatial resolution from becoming lower, without the need to rotate the transducer element groups having the RCA structure. In other words, the ultrasound diagnosis apparatuses according to the embodiments are configured so as to be able to improve the image quality of the ultrasound images obtained by using the transducer element groups having the RCA structure.

Next, the ultrasound diagnosis apparatuses according to the embodiments will be explained, with reference to the accompanying drawings.

First Embodiment

Figure 8:
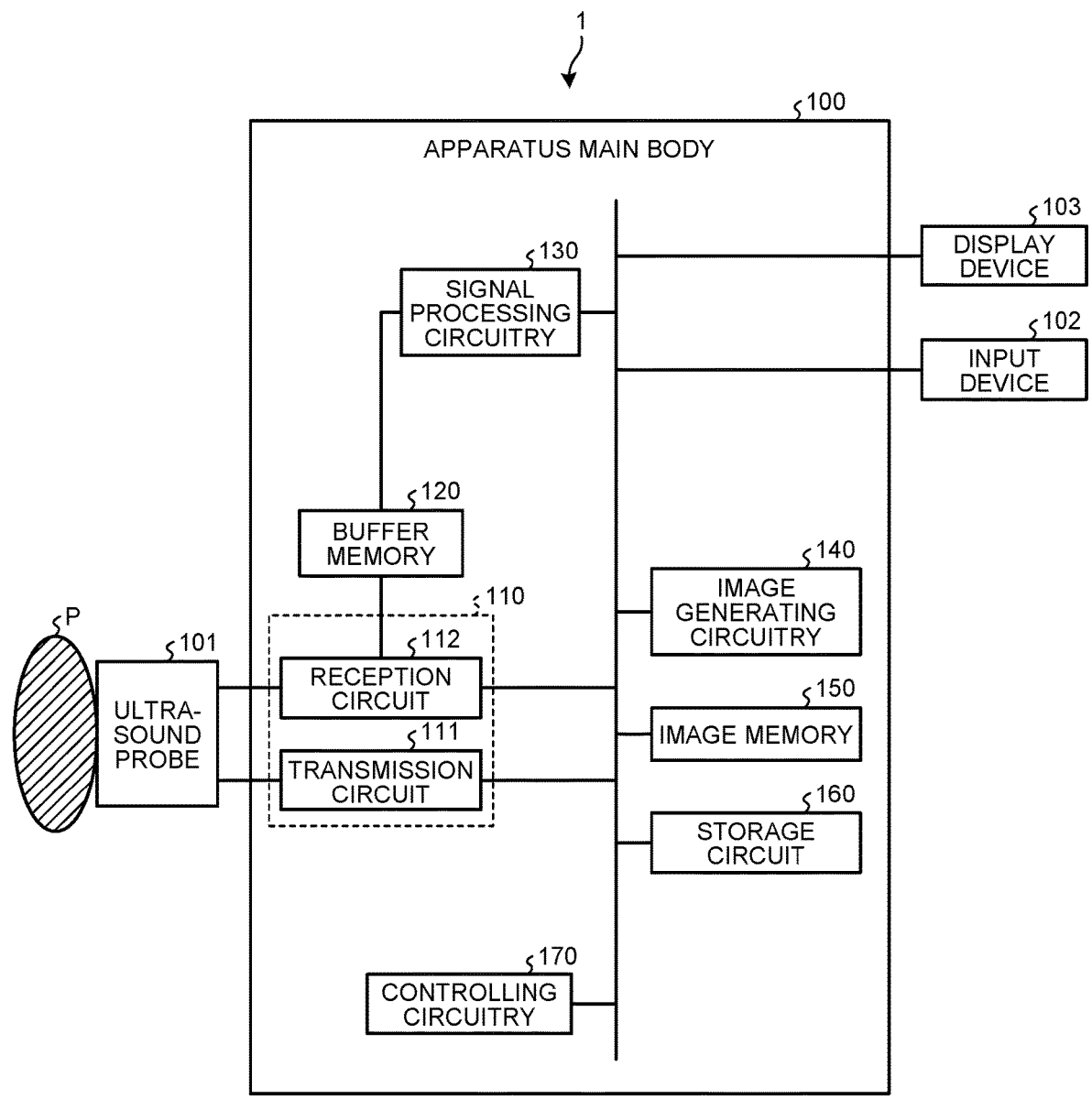
FIG. 8 is a block diagram illustrating an exemplary configuration of an ultrasound diagnosis apparatus according to a first embodiment.

FIG. 8 is a block diagram illustrating an exemplary configuration of an ultrasound diagnosis apparatus 1 according to a first embodiment. As illustrated in FIG. 8, the ultrasound diagnosis apparatus 1 according to the first embodiment includes an apparatus main body 100, an ultrasound probe 101, an input device 102, and a display device 103.

For example, the ultrasound probe 101 includes a plurality of transducer elements (piezoelectric elements). The plurality of transducer elements are configured to generate an ultrasound wave on the basis of a drive signal supplied from a transmission circuit 111 in a transmission and reception circuit 110 included in the apparatus main body 100. More specifically, as a result of the transmission circuit 111 applying voltage (transmission drive voltage), the plurality of transducer elements are configured to generate the ultrasound wave having a waveform corresponding to the transmission drive voltage. The waveform of the transmission drive voltage indicated by the drive signal is the waveform of the voltage applied to the plurality of transducer elements. In other words, the ultrasound probe 101 is configured to transmit the ultrasound wave corresponding to the magnitude of the applied transmission drive voltage. Further, the ultrasound probe 101 is configured to receive a reflected wave from an examined subject (hereinafter, "patient") P, to convert the reflected wave into a reflected-wave signal (a reception signal) realized with an electrical signal, and to output the reflected-wave signal to the apparatus main body 100. Further, for example, the ultrasound probe 101 includes a matching layer provided for the transducer elements, a backing member configured to prevent the ultrasound wave from propagating rearwards from the transducer elements, and the like. In this situation, the ultrasound probe 101 is detachably connected to the apparatus main body 100.

When the ultrasound wave is transmitted from the ultrasound probe 101 to the patient P, the transmitted ultrasound wave is repeatedly reflected on a surface of discontinuity of acoustic impedances at a tissue in the body of the patient P and is received as the reflected wave by the plurality of transducer elements included in the ultrasound probe 101. The amplitude of the received reflected wave is dependent on the difference between the acoustic impedances on the surface of discontinuity on which the ultrasound wave is reflected. When a transmitted ultrasound pulse is reflected on the surface of a moving blood flow, a cardiac wall, or the like, the reflected wave is, due to the Doppler effect, subject to a frequency shift, depending on a velocity component of the moving members with respect to the ultrasound wave transmission direction. Further, the ultrasound probe 101 is configured to output the reflected-wave signal to a reception circuit 112 in the transmission and reception circuit 110 (explained later).

The ultrasound probe 101 can be attached to and detached from the apparatus main body 100. When a two-dimensional region in the patient P is to be scanned (a two-dimensional scan), for example, an operator connects, as the ultrasound probe 101, a one-dimensional (1D) array probe in which the plurality of transducer element are arranged in a single line, to the apparatus main body 100. Examples of different types of 1D array probes include linear ultrasound probes, convex ultrasound probes, and sector ultrasound probes. Further, when a three-dimensional region in the patient P is to be scanned (a three-dimensional scan), for example, the operator connects, as the ultrasound probe 101, a mechanical four-dimensional (4D) probe or a two-dimensional (2D) array probe, to the apparatus main body 100. The mechanical 4D probe is capable of performing a two-dimensional scan by using a plurality of transducer elements arranged in a single line like in the 1D array probe and is also capable of performing a three-dimensional scan by swinging the plurality of transducer elements at a predetermined angle (a swing angle). Further, the 2D array probe is capable of performing a three-dimensional scan by using a plurality of transducer elements arranged in a matrix formation and is also capable of performing a two-dimensional scan by transmitting an ultrasound wave in a converged manner.

Figure 9A:
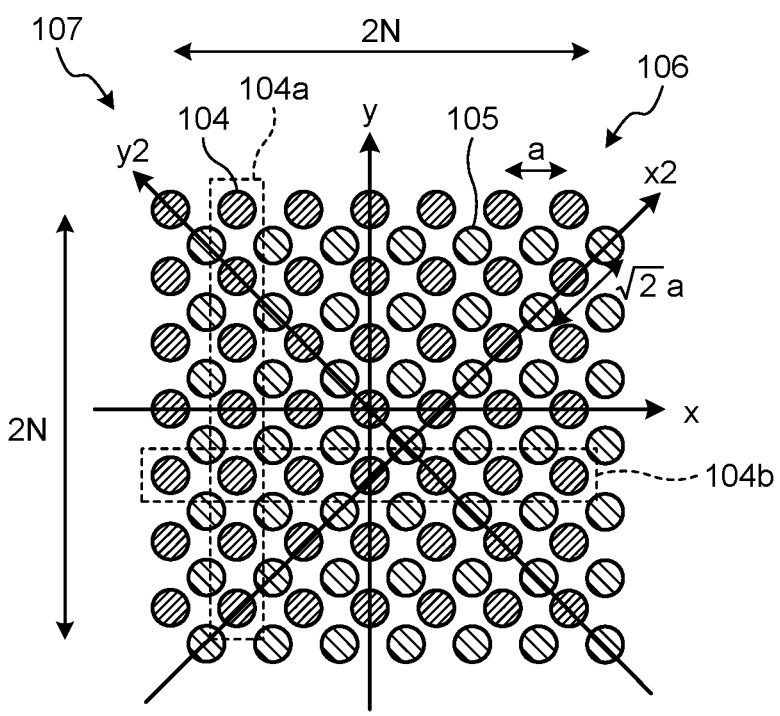
FIG. 9A is a diagram illustrating an exemplary configuration of an ultrasound probe according to the first embodiment.
Figure 9B:
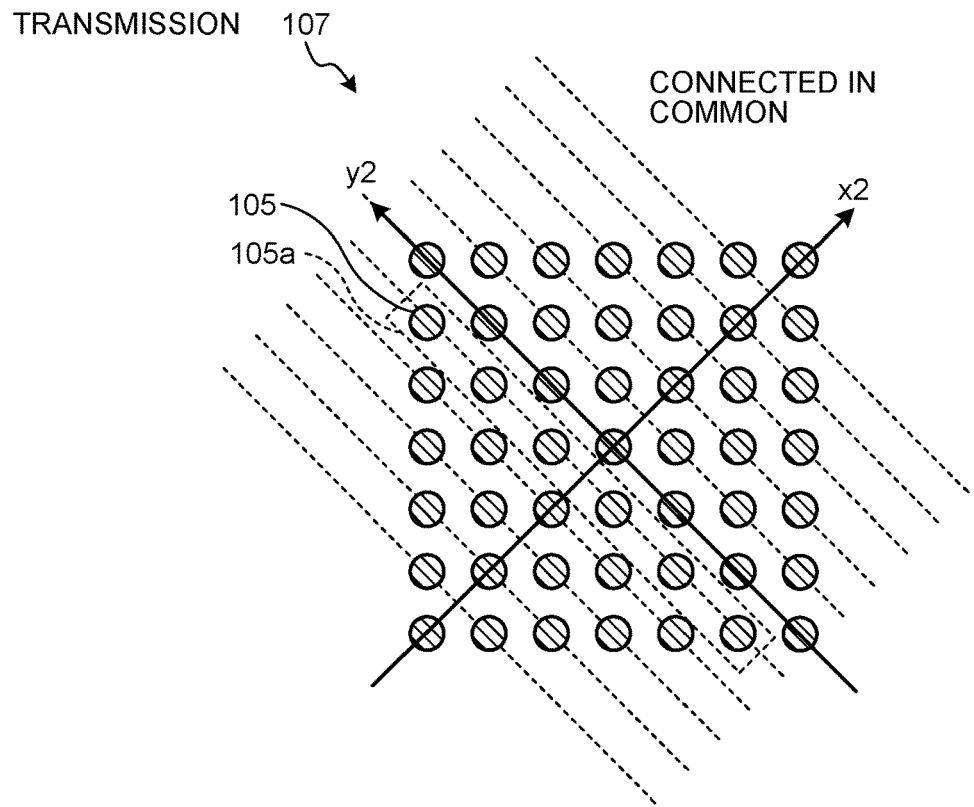
FIG. 9B is another diagram illustrating the exemplary configuration of the ultrasound probe according to the first embodiment.
Figure 9C:
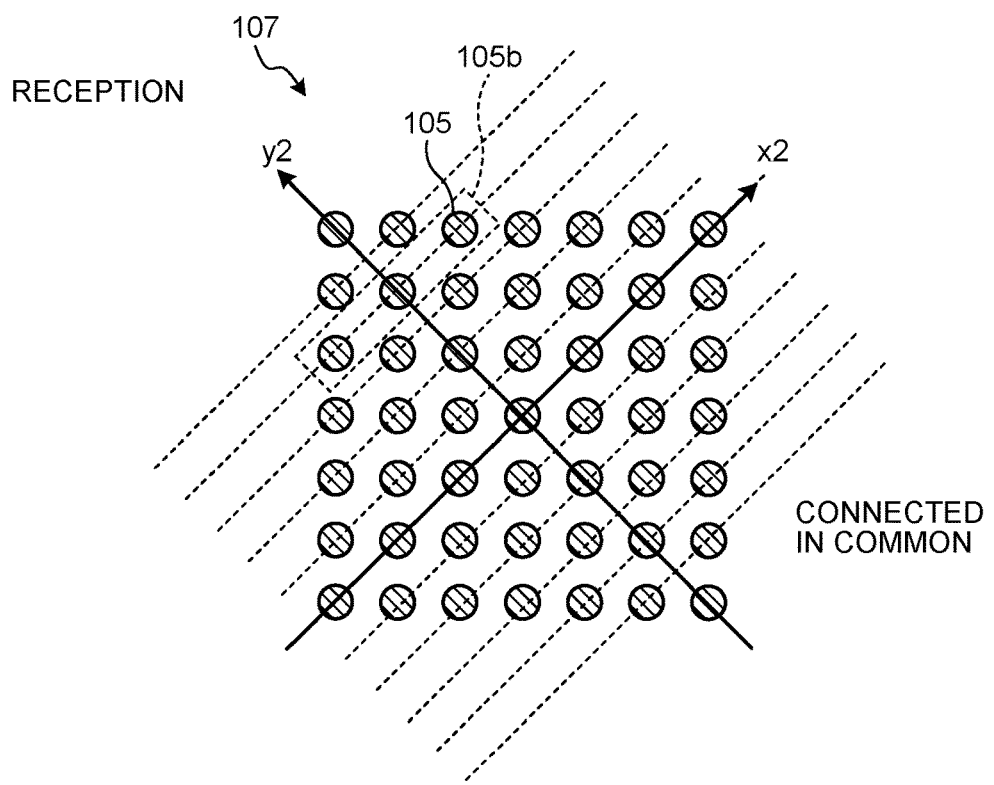
FIG. 9C is yet another diagram illustrating the exemplary configuration of the ultrasound probe according to the first embodiment.

FIGS. 9A to 9C are diagrams illustrating an exemplary configuration of the ultrasound probe 101 according to the first embodiment. As illustrated in FIG. 9A, the ultrasound probe 101 includes a plurality of transducer elements 104 forming a first transducer element group 106 having the RCA structure and a plurality of transducer elements 105 forming a second transducer element group 107 having the RCA structure. In other words, as transducer element groups having the RCA structure, the ultrasound probe 101 includes the two systems of transducer element groups (i.e., the first transducer element group 106 and the second transducer element group 107). For example, in a two-dimensional coordinate system structured with an x-axis and a y-axis, the ultrasound probe 101 includes $N^2$ transducer elements 104 arranged in the formation of N rows in the x-axis direction by N columns in the y-axis direction and $N^2$ transducer elements 105 arranged in the formation of N rows in the x-axis direction by N columns in the y-axis direction. In the example in FIG. 9A, the value of N is 7.

The transducer elements 104 and the transducer elements 105 are configured, for example, by using Micromachined Ultrasound Transducers (MUTs). Examples of the MUTs include Capacitive Micromachined Ultrasound Transducers (CMUTs). Each of the cells of the MUTs corresponds to one transducer element 104 or one transducer element 105.

As illustrated in FIG. 9A, the distance between two transducer elements 104 positioned adjacent to each other in the x-axis direction is "a". Similarly, the distance between two transducer elements 105 positioned adjacent to each other in the x-axis direction is also "a". Further, the distance between two transducer elements 104 positioned adjacent to each other in the y-axis direction and the distance between two transducer elements 105 positioned adjacent to each other in the y-axis direction are each also "a".

The two-dimensional coordinate system structured with the x-axis and the y-axis illustrated in FIG. 9A corresponds to the first transducer element group 106 having the RCA structure. Further, the two-dimensional coordinate system structured with an x2-axis and a y2-axis illustrated in FIG. 9A corresponds to the second transducer element group 107 having the RCA structure. In this situation, the two-dimensional coordinate system structured with the x2-axis and the y2-axis is a coordinate system obtained by translating the two-dimensional coordinate system structured with the x-axis and the y-axis by a/2 in the positive direction on the x-axis and by −a/2 in the negative direction on the y-axis and further rotating the translated two-dimensional coordinate system structured with the x-axis and the y-axis by 45°, on the origin of the two-dimensional coordinate system structured with the x-axis and the y-axis.

Consequently, as illustrated in FIG. 9A, the distance between two transducer elements 105 positioned adjacent to each other in the x2-axis direction is "$2^{1/2}a$". Similarly, the distance between two transducer elements 104 positioned adjacent to each other in the x2-axis direction is also "$2^{1/2}a$". Further, the distance between two transducer elements 104 positioned adjacent to each other in the y2-axis direction and the distance between two transducer elements 105 positioned adjacent to each other in the y2-axis direction are each also "$2^{1/2}a$".

When the first transducer element group 106 having the RCA structure is to perform ultrasound transmission, as illustrated in FIG. 9A, in the ultrasound probe 101, one of the two surfaces (e.g., the front surface) of each of the N transducer elements 104 arranged in the column direction (the y-axis direction) are connected in common to one another. In other words, in the ultrasound probe 101, the N transducer elements 104 arranged in the column direction (the y-axis direction) are connected in common to one another. As a result, while each of the transducer element groups 104a includes the N transducer elements 104 that are connected in series and arranged in the column direction, as many transducer element groups 104a as N are arranged in the row direction (the x-axis direction). In this situation, the N transducer elements 104 arranged in the column direction (the y-axis direction) serve as an example of the plurality of first transducer elements.

Further, when the first transducer element group 106 having the RCA structure is to perform ultrasound (reflected wave) reception, as illustrated in FIG. 9A, in the ultrasound probe 101, the other (e.g., the rear surface) of the two surfaces of each of the N transducer elements 104 arranged in the row direction (the x-axis direction) are connected in common to one another. In other words, in the ultrasound probe 101, the N transducer elements 104 arranged in the row direction (the x-axis direction) are connected in common to one another. As a result, while each of the transducer element groups 104b includes the N transducer elements 104 that are connected in series and arranged in the row direction, as many transducer element groups 104b as N are arranged in the column direction (the y-axis direction). In this situation, the N transducer elements 104 arranged in the row direction (the x-axis direction) serve as an example of the plurality of second transducer elements.

In contrast, when the second transducer element group 107 having the RCA structure is to perform ultrasound transmission, as illustrated in FIG. 9B, in the ultrasound probe 101, one of the two surfaces (e.g., the front surface) of each of k transducer elements 105 (where k=2, 3, . . . N) arranged in the column direction (the y2-axis direction) are connected in common to one another. In other words, in the ultrasound probe 101, the k transducer elements 105 arranged in the column direction (the y2-axis direction) are connected in common to one another. As a result, while each of the transducer element groups 105a includes the k transducer elements 105 that are connected in series and arranged in the column direction, as many transducer element groups 105a as (2N-3) are arranged in the row direction (the x2-axis direction). In this situation, the k transducer elements 105 arranged in the column direction (the y2-axis direction) serve as an example of the plurality of first transducer elements.

Further, when the second transducer element group 107 having the RCA structure is to perform ultrasound (reflected wave) reception, as illustrated in FIG. 9C, in the ultrasound probe 101, the other (e.g., the rear surface) of the two surfaces of each of k transducer elements 105 arranged in the row direction (the x2-axis direction) are connected in common to one another. In other words, in the ultrasound probe 101, the k transducer elements 105 arranged in the row direction (the x2-axis direction) are connected in common to one another. As a result, while each of the transducer element groups 105b includes the k transducer elements 105 that are connected in series and arranged in the row direction, as many transducer element groups 105b as (2N-3) are arranged in the column direction (the y2-axis direction). In this situation, the k transducer elements 105 arranged in the row direction (the x2-axis direction) serve as an example of the plurality of second transducer elements.

As explained above, the ultrasound probe 101 according to the first embodiment includes the plurality of transducer elements 104 and 105 arranged two-dimensionally. Further, the ultrasound probe 101 includes the plurality of transducer element groups (the first transducer element group 106 and the second transducer element group 107) of the Row-Column Addressing type in which, when the ultrasound transmission is to be performed, either the N transducer elements 104 or the k transducer elements 105 that are arranged in the direction (e.g., the column direction in the above example) of one of the two axes (e.g., the x- and y-axes or the x2- and y2-axes) intersecting each other are connected in common to one another and in which, when the ultrasound reception is to be performed, either the N transducer elements 104 or the k transducer elements 105 that are arranged in the direction (e.g., the row direction in the above example) of the other of the two axes are connected in common to one another.

Further, in the first embodiment, the plurality of sets each made up of two axes (e.g., the set made up of the x- and y-axes and the set made up of the x2- and y2-axes) corresponding to the plurality of transducer element groups (the first transducer element group 106 and the second transducer element group 107) of the Row-Column Addressing type are mutually different. More specifically, for example, the set made up of the x2- and y2-axes is different from the set made up of the x- and y-axes by a 45-degree angle.

Further, in the first embodiment, the ultrasound probe 101 includes the plurality of transducer element groups (the first transducer element group 106 and the second transducer element group 107) of the Row-Column Addressing type configured so that the product of the angular interval (e.g., 45°) between the plurality of sets each made up of two axes (e.g., the set made up of the x- and y-axes and the set made up of the x2- and y2-axes) corresponding to the plurality of transducer element groups (the first transducer element group 106 and the second transducer element group 107) of the Row-Column Addressing type and the quantity (e.g., 2) of the plurality of transducer element groups of the Row-Column Addressing type is 90°.

For example, the input device 102 is realized by using input means such as a mouse, a keyboard, a button, a panel switch, a touch command screen, a foot switch, a trackball, a joystick, and/or the like. The input device 102 is configured to receive various types of setting requests from the operator of the ultrasound diagnosis apparatus 1 and to transfer the received various types of setting requests to the apparatus main body 100.

For example, the display device 103 is configured to display a Graphical User Interface (GUI) used by the operator of the ultrasound diagnosis apparatus 1 for inputting the various types of setting requests via the input device 102 and to display an ultrasound image based on the ultrasound image data generated in the apparatus main body 100, and the like. The display device 103 is realized by using a liquid crystal monitor, a Cathode Ray Tube (CRT) monitor, or the like. The display device 103 is an example of a display unit.

Figure 1A:
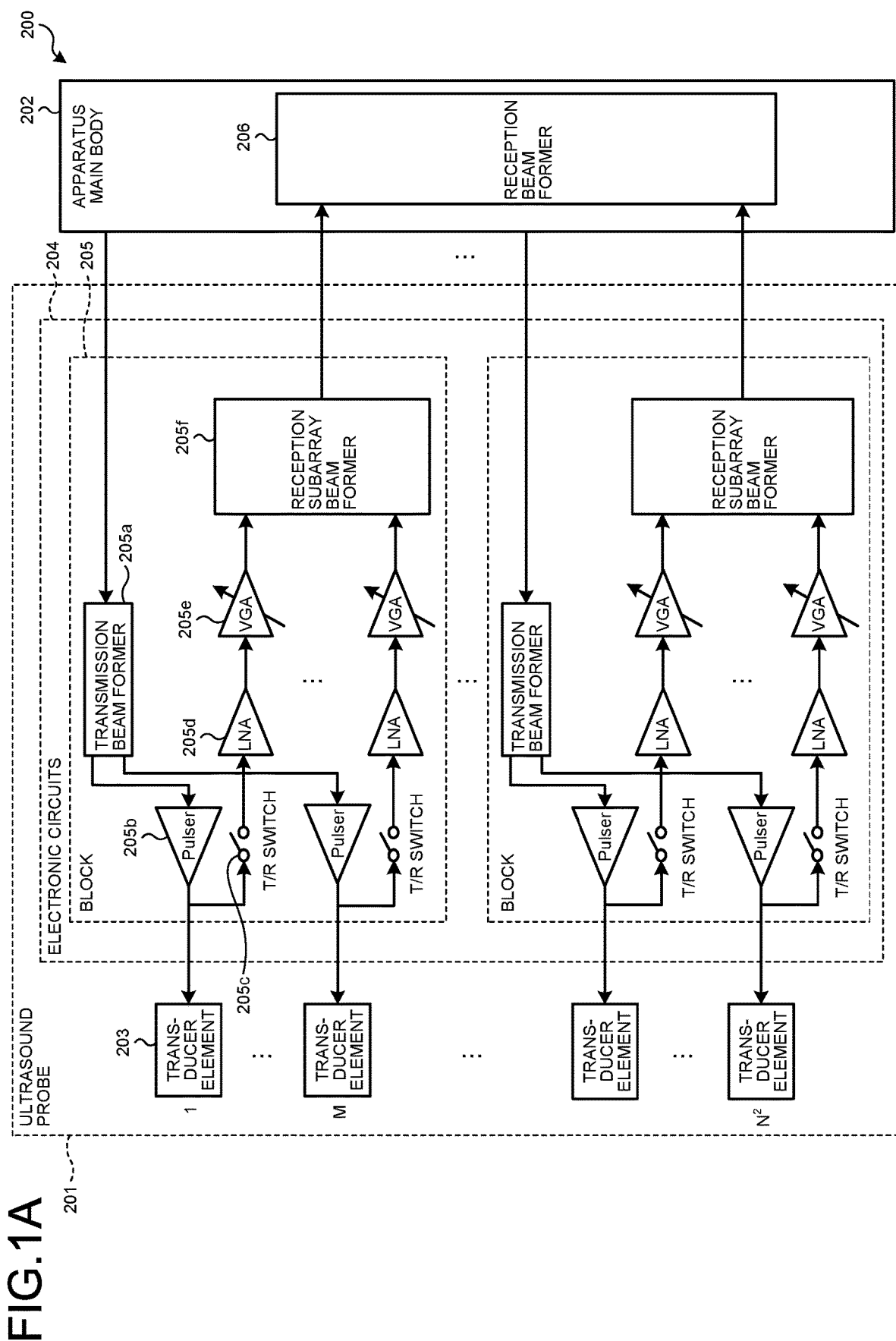
FIG. 1A is a diagram illustrating an exemplary configuration of a conventional ultrasound diagnosis apparatus.
Figure 1B:
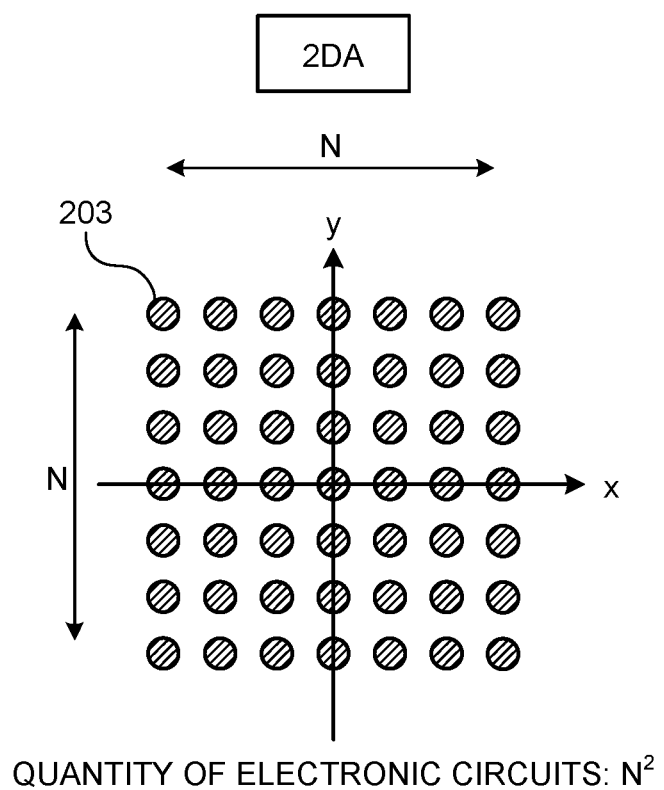
FIG. 1B is a diagram illustrating an exemplary configuration of a conventional ultrasound probe.
Figure 2A:
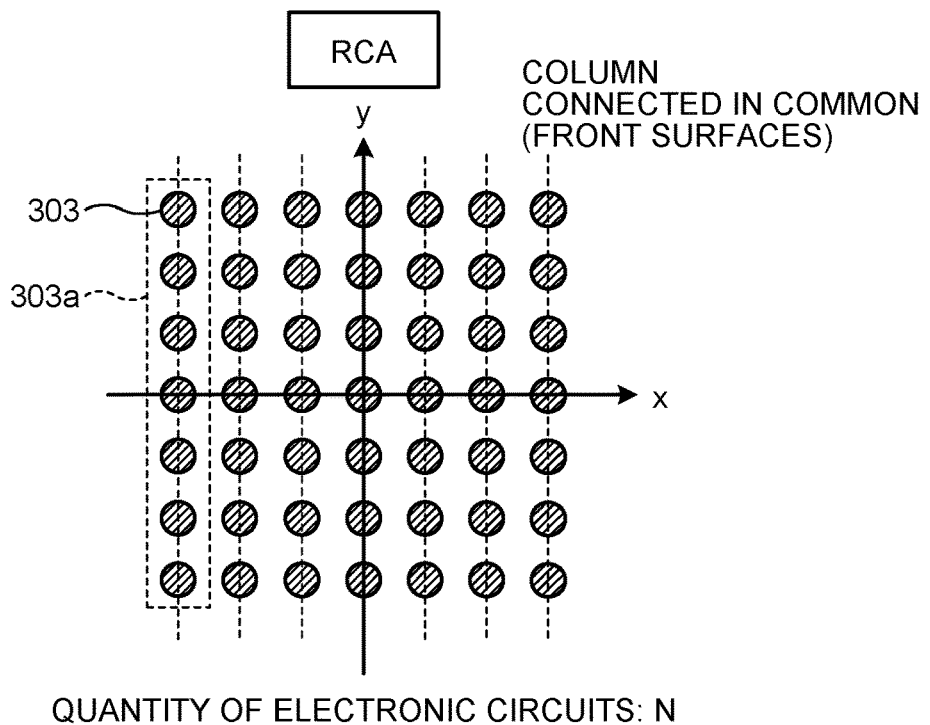
FIG. 2A is a drawing for explaining an example of an RCA scheme.
Figure 2B:
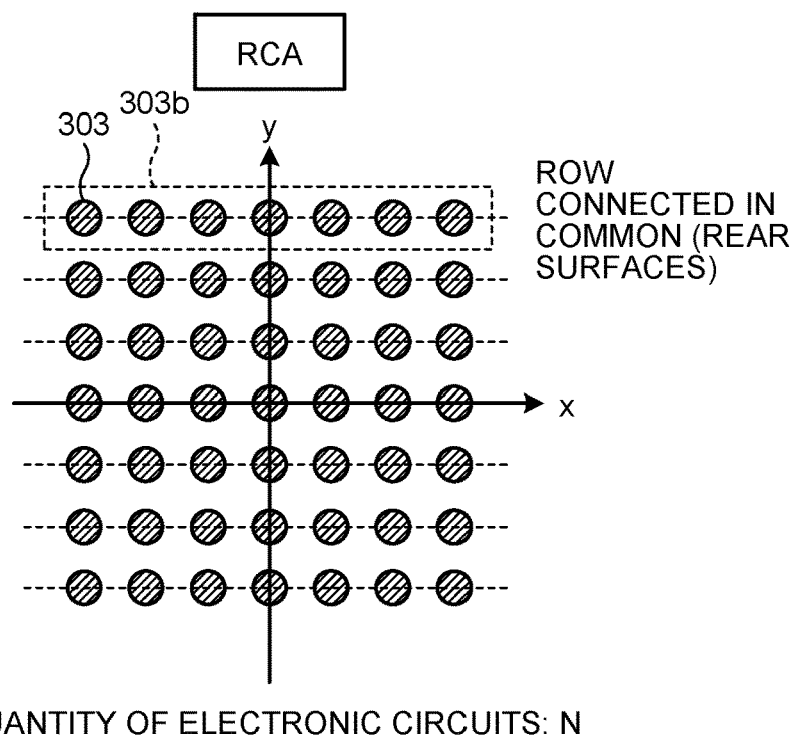
FIG. 2B is another drawing for explaining the example of the RCA scheme.
Figure 3:
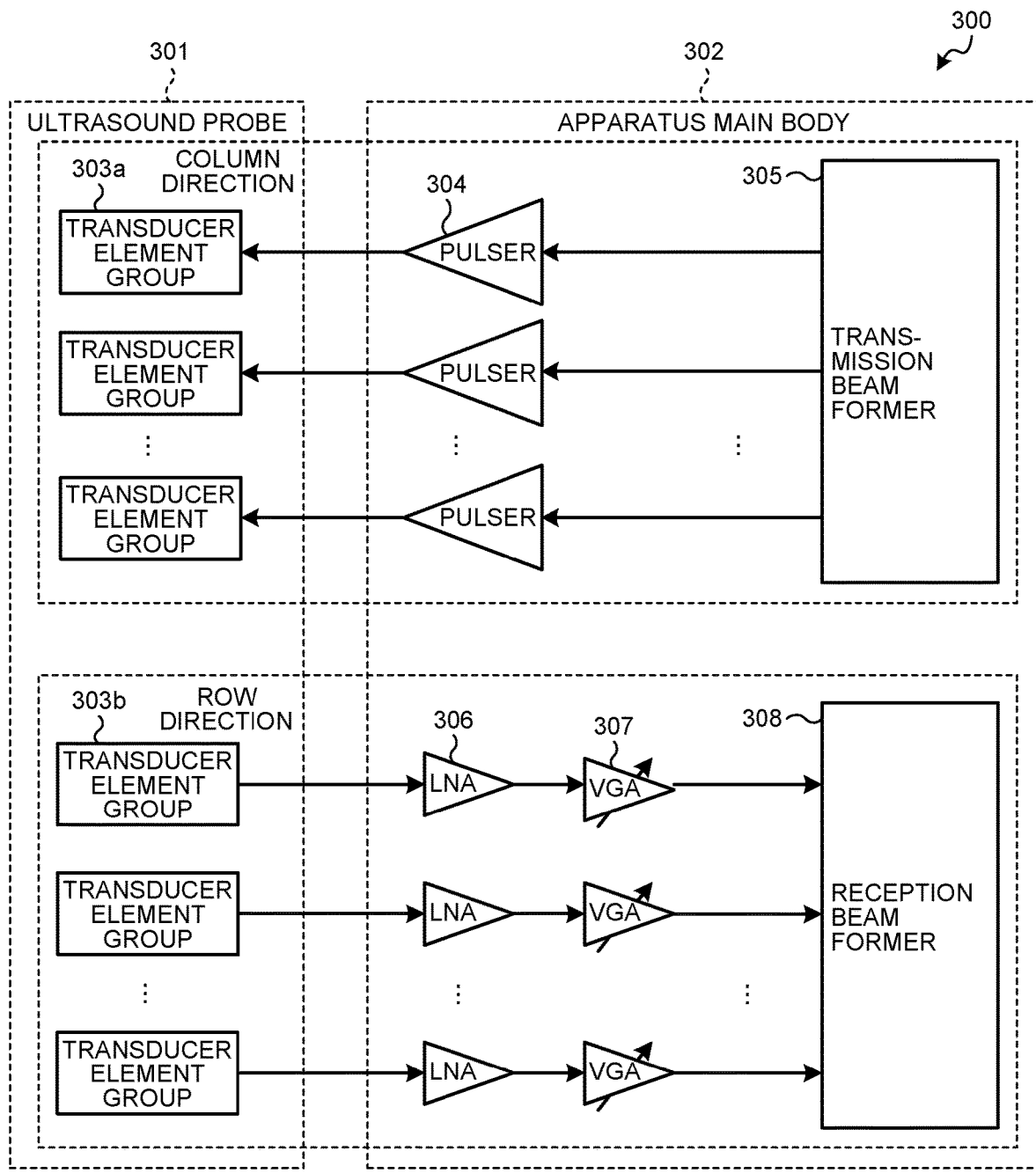
FIG. 3 is a diagram illustrating an exemplary configuration of a conventional ultrasound diagnosis apparatus having a structure of the example of the RCA scheme explained with reference to FIGS. 2A and 2B.

The apparatus main body 100 is configured to generate the ultrasound image data on the basis of the reflected-wave signal transmitted thereto from the ultrasound probe 101. In this situation, the ultrasound image data is an example of image data. The apparatus main body 100 is capable of generating two-dimensional ultrasound image data on the basis of the reflected-wave signal corresponding to a two-dimensional region of the patient P and having been transmitted thereto from the ultrasound probe 101. Further, the apparatus main body 100 is capable of generating three-dimensional ultrasound image data on the basis of the reflected-wave signal corresponding to a three-dimensional region of the patient P and having been transmitted thereto from the ultrasound probe 101. As illustrated in FIG. 1, the apparatus main body 100 includes the transmission and reception circuit 110, a buffer memory 120, signal processing circuitry 130, image generating circuitry 140, an image memory 150, a storage circuit 160, and controlling circuitry 170.

Under control of the controlling circuitry 170, the transmission and reception circuit 110 is configured to cause the ultrasound probe 101 to transmit an ultrasound wave and to cause the ultrasound probe 101 to receive a reflected wave of the ultrasound wave. In other words, the transmission and reception circuit 110 is configured to perform a scan via the ultrasound probe 101. The scan may be referred to as scanning, an ultrasound scan, or an ultrasonic scan. The transmission and reception circuit 110 is an example of a transmission and reception unit. The transmission and reception circuit 110 includes the transmission circuit 111 and the reception circuit 112.

Figure 10:
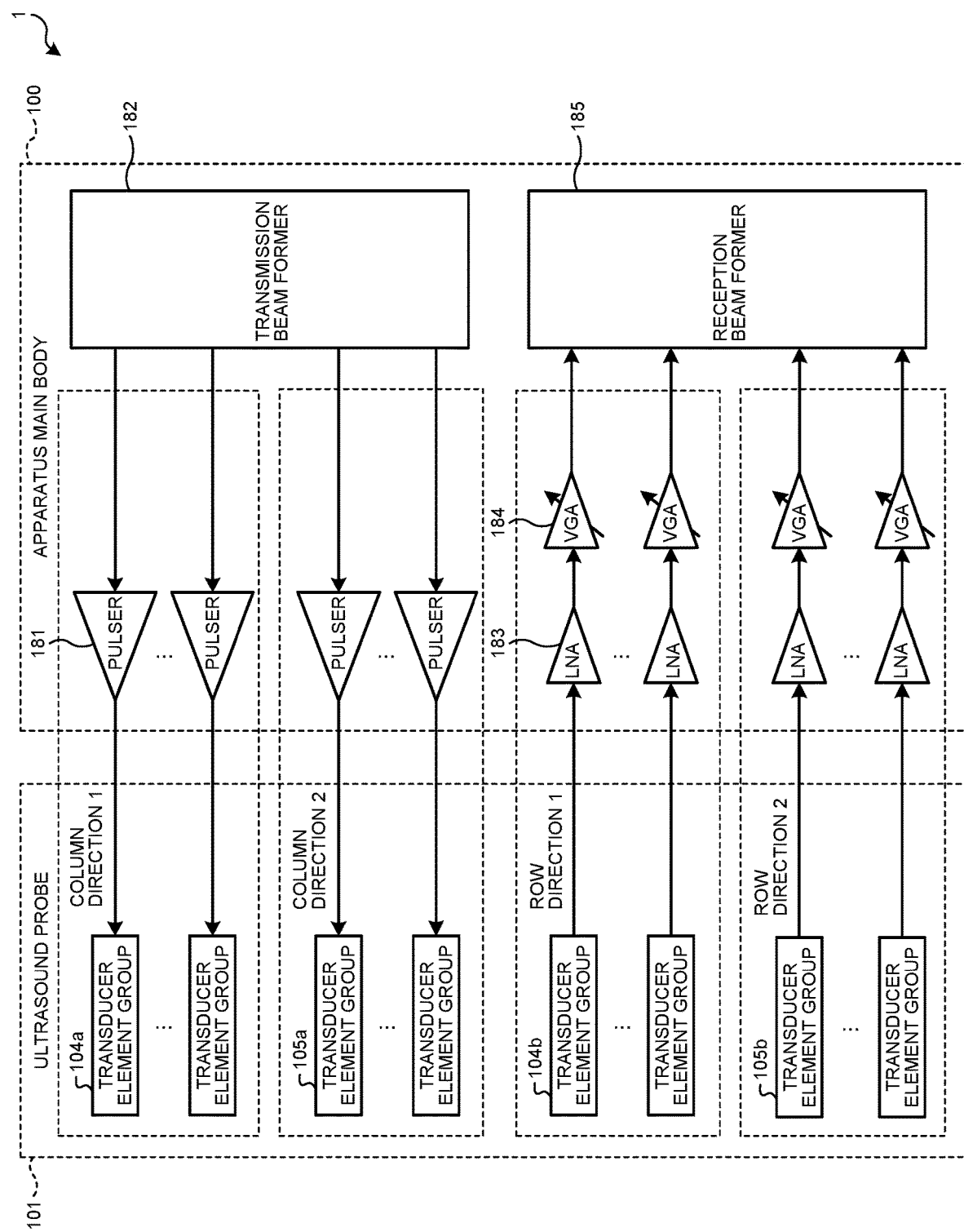
FIG. 10 is a diagram illustrating an exemplary configuration of a transmission and reception system of the ultrasound diagnosis apparatus according to the first embodiment.

Under the control of the controlling circuitry 170, the transmission circuit 111 is configured to cause the ultrasound wave to be transmitted from the ultrasound probe 101. Under the control of the controlling circuitry 170, the transmission circuit 111 is configured to supply the drive signal to the ultrasound probe 101. When a two-dimensional region in the patient P is to be scanned, the transmission circuit 111 is configured to cause the ultrasound probe 101 to transmit an ultrasound beam for scanning the two-dimensional region. In contrast, when a three-dimensional region in the patient P is to be scanned, the transmission circuit 111 is configured to cause the ultrasound probe 101 to transmit an ultrasound beam for scanning the three-dimensional region. FIG. 10 is a diagram illustrating an exemplary configuration of a transmission and reception system of the ultrasound diagnosis apparatus 1 according to the first embodiment.

As illustrated in FIG. 10, the transmission circuit 111 includes pulsers 181 and a transmission beam former 182. Via the pulsers 181, the transmission beam former 182 is configured to cause a delay-controlled ultrasound wave to be transmitted from each of the plurality of transducer elements 104 included in the transducer element groups 104a and each of the plurality of transducer elements 105 included in the transducer element groups 105a.

The transmission beam former 182 includes a rate pulser generating circuit and a transmission delay circuit. The rate pulser generating circuit is configured to repeatedly generate a rate pulse for forming a transmission ultrasound wave (a transmission beam) at a predetermined rate frequency (a Pulse Repetition Frequency [PRF]). As a result of the rate pulse being routed through the transmission delay circuit, voltage is applied to the pulsers 181 while having mutually-different transmission delay time periods. For example, the transmission delay circuit is configured to apply the transmission delay time period that corresponds to each of the transducer elements and is required to converge the ultrasound wave generated from the ultrasound probe 101 into the form of a beam and to determine transmission directionality, to each of the rate pulses generated by the rate pulser generating circuit.

Each of the pulsers 181 is configured to supply the delay-controlled drive signal (a drive pulse) to the transducer elements. Each of the pulsers 181 is configured to supply the drive signal to the ultrasound probe 101 with timing based on the rate pulses. In other words, each of the pulsers 181 is configured to apply voltage (transmission drive voltage) having a waveform indicated by the drive signal to the ultrasound probe 101, with the timing based on the rate pulses. The transmission delay circuit is configured to arbitrarily adjust the transmission direction of the ultrasound wave transmitted from the transmission surfaces of the transducer elements 104 and 105, by varying the transmission delay time period applied to each of the rate pulses.

The drive pulse travels from each of the pulsers 181 and reaches the transducer elements 104 and 105 in the ultrasound probe 101 via a cable and is subsequently converted at the transducer elements 104 and 105 from an electrical signal into mechanical vibration. In other words, as a result of the voltage being applied to the transducer elements 104 and 105, the transducer elements 104 and 105 are configured to mechanically vibrate. The ultrasound wave generated by the mechanical vibration is transmitted to the inside of the patient P, i.e., to the inside of the patient's body. In this situation, ultrasound waves having mutually-different transmission delay periods in correspondence with the transducer elements 104 and 105 are converged so as to propagate in a predetermined direction.

Further, under the control of the controlling circuitry 170, the transmission circuit 111 has a function capable of instantaneously changing the transmission frequency, the transmission drive voltage, and the like for executing a predetermined scan sequence. In particular, the capability to change the transmission drive signal is realized by a transmission circuit of a linear amplifier type capable of instantaneously switching the value of the transmission drive voltage or a mechanism configured to electrically switch between a plurality of power source units.

In the first embodiment, as illustrated in FIG. 10, one pulser 181 is provided for each of the N transducer element groups 104a and each of the (2N-3) transducer element groups 105a. Accordingly, the apparatus main body 100 includes as many pulsers 181 as (3N-3). Consequently, when each of the pulsers 181 is regarded as one electronic circuit, the apparatus main body 100 needs 2N electronic circuits when the ultrasound diagnosis apparatus 1 performs ultrasound transmission.

When the first transducer element group 106 is to perform ultrasound transmission, the transmission beam former 182 is configured, via a corresponding one of the pulsers 181, to cause an ultrasound wave to which a transmission delay is applied in the x-axis direction to be transmitted from the other surfaces (e.g., the rear surfaces) of the N transducer elements 104 included in the transducer element group 104a. The transmission beam former 182 is configured to perform this process for each of the transducer element groups 104a.

Further, when the second transducer element group 107 is to perform ultrasound transmission, the transmission beam former 182 is configured, via a corresponding one of the pulsers 181, to cause an ultrasound wave to which a transmission delay is applied in the x2-axis direction to be transmitted from the other surfaces (e.g., the rear surfaces) of the k transducer elements 105 included in the transducer element group 105a. The transmission beam former 182 is configured to perform this process for each of the transducer element groups 105a.

The reflected wave of the ultrasound wave transmitted by the ultrasound probe 101 reaches the transducer elements provided inside the ultrasound probe 101 and is subsequently converted at the transducer elements 104 and 105 from mechanical vibration into an electrical signal (a reflected-wave signal) so as to be input to the reception circuit 112. As illustrated in FIG. 10, the reception circuit 112 includes LNAs 183, VGAs 184, an Analog-to-Digital (A/D) converter (not illustrated), a reception beam former 185, and the like and is configured to generate reflected-wave data by performing various types of processes on the reflected-wave signal transmitted thereto from the ultrasound probe 101. The abovementioned reflected-wave signal and reflected-wave data serve as examples of reception signals. The reception circuit 112 is configured to generate two-dimensional reflected-wave data from a two-dimensional reflected-wave signal transmitted thereto from the ultrasound probe 101. Further, the reception circuit 112 is configured to generate three-dimensional reflected-wave data from a three-dimensional reflected-wave signal transmitted thereto from the ultrasound probe 101. Further, the reception circuit 112 is configured to store the generated reflected-wave data into the buffer memory 120.

When the first transducer element group 106 having the RCA structure has received an ultrasound wave (a reflected wave), each of the LNAs 183 is configured to amplify the reflected-wave signal output from the transducer element group 104b. In this situation, the reflected-wave signal output from any one of the transducer element groups 104b is a reflected-wave signal (a reception signal) obtained by adding up (combining) the N reflected-wave signals output from the N transducer elements 104 included in the transducer element group 104b. As described herein, as a result of the first transducer element group 106 having the RCA structure transmitting and receiving the ultrasound wave, each of the transducer element groups 104b is configured to output the reflected-wave signal obtained by adding up the N reflected-wave signals, to the corresponding LNA 183.

Further, when the second transducer element group 107 having the RCA structure has received an ultrasound wave (a reflected wave), each of the LNAs 183 is configured to amplify the reflected-wave signal output from the transducer element group 105b. In this situation, the reflected-wave signal output from any one of the transducer element groups 105b is a reflected-wave signal obtained by adding up (combining) the k reflected-wave signals output from the k transducer elements 105 included in the transducer element group 105b. As described herein, as a result of the second transducer element group 107 having the RCA structure transmitting and receiving the ultrasound wave, each of the transducer element groups 105b is configured to output the reflected-wave signal obtained by adding up the k reflected-wave signals, to the corresponding LNA 183.

Further, each of the VGAs 184 is configured to adjust gain of the amplified reflected-wave signal, in accordance with depth. Further, the Analog-to-Digital (A/D) converter is configured to convert the reflected-wave signal being the gain-adjusted signal in an analog format (an analog signal), into a reflected-wave signal in a digital format (a digital signal).

After that, the reception beam former 185 is configured to apply a reception delay to the N gain-adjusted reflected-wave signals (the digital signals) output from the N transducer element groups 104b and to add up the N reflected-wave signals to which the reception delay was applied. Further, the reception beam former 185 is configured to store the reflected-wave data obtained by adding up the N reflected-wave signals, into the buffer memory 120. The reflected-wave data obtained as a result of the first transducer element group 106 having the RCA structure transmitting and receiving the ultrasound wave in this manner may hereinafter be referred to as "first reflected-wave data".

Further, the reception beam former 185 is configured to apply a reception delay to the (2N-3) gain-adjusted reflected-wave signals (the digital signals) output from the (2N-3) transducer element groups 105b and to add up the (2N-3) reflected-wave signals to which the reception delay was applied. Further, the reception beam former 185 is configured to store the reflected-wave data obtained by adding up the (2N-3) reflected-wave signals, into the buffer memory 120. The reflected-wave data obtained as a result of the second transducer element group 107 having the RCA structure transmitting and receiving the ultrasound wave in this manner may hereinafter be referred to as "second reflected-wave data".

Accordingly, with respect to each of the plurality of transducer element groups (the first transducer element group 106 and the second transducer element group 107), the reception circuit 112 is configured to perform the beam forming process (the reception beam forming process) on the plurality of reflected-wave signals output from the plurality of transducer elements 104 or the plurality of transducer elements 105.

In the present example, in the first embodiment, as illustrated in FIG. 10, one LNA 183 and one VGA 184 are provided for each of the N transducer element groups 104b and each of the (2N-3) transducer element groups 105b. Accordingly, the apparatus main body 100 includes as many LNAs 183 as (3N-3) and as many VGAs 184 as (3N-3). Consequently, when a set made up of one LNA 183 and one VGA 184 is regarded as one electronic circuit, the apparatus main body 100 needs (3N-3) electronic circuits when the ultrasound diagnosis apparatus 1 performs ultrasound transmission.

The buffer memory 120 is a memory configured to temporarily store therein the reflected-wave data generated by the transmission and reception circuit 110. For example, the buffer memory 120 is configured so as to be able to store therein reflected-wave data corresponding to a predetermined number of frames. Further, while having stored therein the reflected-wave data corresponding to the predetermined number of frames, when reflected-wave data corresponding to one frame is newly generated by the reception circuit 112, the buffer memory 120 is configured, under control of the reception circuit 112, to discard the reflected-wave data corresponding to one frame generated earliest and to store therein the newly-generated reflected-wave data corresponding to the one frame. For example, the buffer memory 120 is realized by using a semiconductor memory element such as a Random Access Memory (RAM) or a flash memory.

The signal processing circuitry 130 is configured to read the first reflected-wave data and the second reflected-wave data from the buffer memory 120. Further, the signal processing circuitry 130 is configured to add the read second reflected-wave data to the read first reflected-wave data, to further perform various types of signal processing processes on data obtained by performing the addition (data resulting from the addition), and to output the data resulting from the addition on which the various types of signal processing processes were performed to the image generating circuitry 140 as B-mode data or Doppler data. For example, the signal processing circuitry 130 is realized by using a processor. The signal processing circuitry 130 is an example of a signal processing unit.

Figure 11:
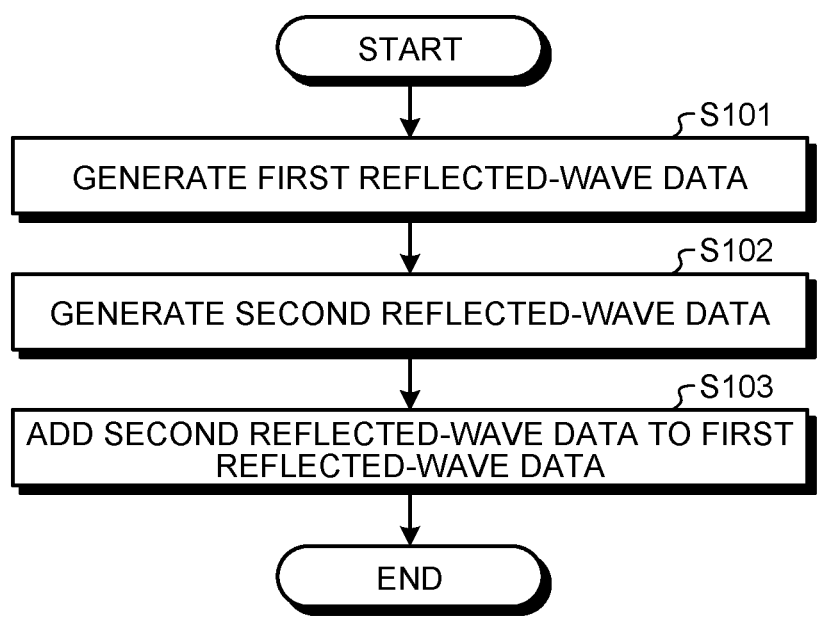
FIG. 11 is a flowchart illustrating a flow in an example of processes from when a reception circuit and signal processing circuitry according to the first embodiment generate first reflected-wave data and second reflected-wave data until when data resulting from addition is obtained.

FIG. 11 is a flowchart illustrating a flow in an example of processes from when the reception circuit 112 and the signal processing circuitry 130 according to the first embodiment generate the first reflected-wave data and the second reflected-wave data until when the data resulting from the addition is obtained.

As illustrated in FIG. 1, the reception circuit 112 generates the first reflected-wave data and stores the first reflected-wave data into the buffer memory 120 (step S101). Further, the reception circuit 112 generates the second reflected-wave data and stores the second reflected-wave data into the buffer memory 120 (step S102).

After that, the signal processing circuitry 130 reads the first reflected-wave data and the second reflected-wave data from the buffer memory 120 and adds the second reflected-wave data to the first reflected-wave data (step S103) and ends the processes presented in FIG. 11. In this situation, as explained above, the signal processing circuitry 130 generates the B-mode data or the Doppler data, by performing the various types of signal processing processes on the data resulting from the addition which was obtained by performing the addition.

For example, every time first reflected-wave data and second reflected-wave data corresponding to one frame is newly stored in the buffer memory 120, the signal processing circuitry 130 is configured to read the first reflected-wave data and the second reflected-wave data that correspond to the one frame and were newly stored in the buffer memory 120. Further, every time first reflected-wave data and second reflected-wave data corresponding to one frame are read, the signal processing circuitry 130 is configured to generate data corresponding to the one frame and resulting from addition, by adding the second reflected-wave data to the first reflected-wave data. Further, every time data corresponding to one frame and resulting from the addition is generated, the signal processing circuitry 130 is configured to newly generate B-mode data or Doppler data corresponding to the one frame, by performing the various types of signal processing processes on the data resulting from the addition. Further, every time B-mode data or Doppler data corresponding to one frame is generated, the signal processing circuitry 130 is configured to output the newly-generated B-mode data or Doppler data corresponding to the one frame, to the image generating circuitry 140. Next, examples of the various types of signal processing processes performed by the signal processing circuitry 130 will be explained.

For example, the signal processing circuitry 130 is configured to generate B-mode data in which signal intensities (amplitude intensities) corresponding to sampling points are expressed as levels of brightness, by performing a quadrature detection and performing a logarithmic amplification process and an envelope detecting process, or the like on the data resulting from the addition. After that, the signal processing circuitry 130 is configured to output the generated B-mode data to the image generating circuitry 140.

Further, the signal processing circuitry 130 is configured to perform a signal processing process on the data resulting from the addition, so as to realize harmonic imaging by which a higher harmonic component is visualized in an image. Examples of the harmonic imaging include Contrast Harmonic Imaging (CHI) and Tissue Harmonic Imaging (THI). Further, for the contrast harmonic imaging and the tissue harmonic imaging, scanning methods as follows are known. Examples of the known scanning methods include: Amplitude Modulation (AM) methods, Phase Modulation (PM) methods called a pulse subtraction method and a pulse inversion method, and AMPM methods in which advantageous effects of both the AM and the PM methods are achieved by combining the AM and the PM methods together.

Further, the signal processing circuitry 130 is configured to extract movement information of moving members (a blood flow, a tissue, a contrast agent echo component, etc.) based on the Doppler effect from the data resulting from the addition, by performing a frequency analysis on the data resulting from the addition and to generate Doppler data indicating the extracted movement information. For example, the signal processing circuitry 130 is configured to generate the Doppler data indicating the extracted movement information of the moving members, by extracting, as the movement information of the moving members, an average velocity value, an average dispersion value, an average power value, and the like with respect to multiple points. The signal processing circuitry 130 is configured to output the generated Doppler data to the image generating circuitry 140.

By using the functions of the signal processing circuitry 130 described above, the ultrasound diagnosis apparatus 1 according to the embodiment is capable of implementing a color Doppler method which may be called a Color Flow Mapping (CFM) method. According to the color flow mapping method, ultrasound wave transmission and reception is performed multiple times on a plurality of scanning lines. Further, according to the color flow mapping method, a signal (a blood flow signal) derived from a blood flow is extracted from a data sequence corresponding to mutually the same position, while suppressing signals (clutter signals) derived from stationary tissues or slow-moving tissues, by applying a Moving Target Indicator (MTI) filter to the data sequence corresponding to mutually the same position. Further, according to the color flow mapping method, blood flow information such as velocity of the blood flow, dispersion of the blood flow, power of the blood flow, and the like are estimated on the basis of the blood flow signal. The signal processing circuitry 130 is configured to output color image data indicating the blood flow information estimated by implementing the color flow mapping method, to the image generating circuitry 140. The color image data is an example of Doppler data.

The signal processing circuitry 130 is capable of processing both two-dimensional data resulting from the addition and three-dimensional data resulting from the addition.

The image generating circuitry 140 is configured to generate ultrasound image data from the B-mode data or the Doppler data output from the signal processing circuitry 130. The image generating circuitry 140 is realized by using a processor.

For example, the image generating circuitry 140 is configured to generate two-dimensional B-mode image data in which the intensities of the reflected wave are expressed with brightness levels, from two-dimensional B-mode data generated by the signal processing circuitry 130. Further, the image generating circuitry 140 is configured to generate two-dimensional Doppler image data in which the movement information or the blood flow information is visualized in an image, from two-dimensional Doppler data generated by the signal processing circuitry 130. In this situation, the two-dimensional Doppler image data obtained by visualizing the movement information in the image is velocity image data, dispersion image data, power image data, or image data combining together these types of image data.

In this situation, generally speaking, the image generating circuitry 140 is configured to convert (by performing a scan convert process) a scanning line signal sequence from an ultrasound scan into a scanning line signal sequence in a video format used by television, for example, and to generate display-purpose ultrasound image data. For example, the image generating circuitry 140 is configured to generate the display-purpose ultrasound image data by performing a coordinate transformation process compliant with the ultrasound scanning mode used by the ultrasound probe 101 on the data output from the signal processing circuitry 130. Further, as various types of image processing processes besides the scan convert process, the image generating circuitry 140 is configured to perform, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuitry 140 is configured to combine text information of various types of parameters, scale graduations, body marks, and the like with the ultrasound image data.

Further, the image generating circuitry 140 is configured to generate three-dimensional B-mode image data by performing a coordinate transformation process on three-dimensional B-mode data generated by the signal processing circuitry 130. Further, the image generating circuitry 140 is configured to generate three-dimensional Doppler image data by performing a coordinate transformation process on three-dimensional Doppler data generated by the signal processing circuitry 130. In other words, the image generating circuitry 140 is configured to generate the "three-dimensional B-mode image data and three-dimensional Doppler image data" as "three-dimensional ultrasound image data (volume data)". Further, the image generating circuitry 140 is configured to perform various types of rendering processes on the volume data, so as to generate various types of two-dimensional image data used for displaying the volume data on the display device 103.

Examples of the rendering processes performed by the image generating circuitry 140 include a process of generating Multi Planar Reconstruction (MPR) image data from the volume data by using a Multi Planar Reconstruction (MPR) method. Further, other examples of the rendering processes performed by the image generating circuitry 140 include a Volume Rendering (VR) process by which two-dimensional image data reflecting three-dimensional information is generated. The image generating circuitry 140 is an example of an image generating unit.

The B-mode data and the Doppler data are each ultrasound image data before the scan convert process. The data generated by the image generating circuitry 140 is the display-purpose ultrasound image data after the scan convert process. The B-mode data and the Doppler data may be referred to as raw data.

As explained above, with respect to each of the plurality of transducer element groups (the first transducer element group 106 and the second transducer element group 107), the reception circuit 112, the signal processing circuitry 130, and the image generating circuitry 140 are configured to perform the beam forming process on the plurality of reflected-wave signals output from the plurality of transducer elements 104 or the plurality of transducer elements 105 and to generate the ultrasound image data on the basis of the reflected-wave data obtained from the beam forming processes. The reception circuit 112, the signal processing circuitry 130, and the image generating circuitry 140 serve as an example of a generating unit. In this situation, with respect to each of the plurality of transducer element groups (the first transducer element group 106 and the second transducer element group 107), the reception circuit 112 is configured to perform the beam forming process on the plurality of reception signals output from the plurality of transducer elements 104 or the plurality of transducer elements 105, without implementing apodization.

Further, the signal processing circuitry 130 and the image generating circuitry 140 are configured to add up the plurality of pieces of reflected-wave data (the first reflected-wave data and the second reflected-wave data) generated with respect to the plurality of transducer element groups (the first transducer element group 106 and the second transducer element group 107) and obtained from the plurality of beam forming processes and is further configured to generate the ultrasound image data on the basis of the data resulting from the addition. In this situation, the data resulting from the addition is an example of a signal resulting from the addition.

The image memory 150 is a memory configured to store therein various types of image data generated by the image generating circuitry 140. Further, the image memory 150 is also configured to store therein the data generated by the signal processing circuitry 130. An operator is able to invoke the B-mode data and the Doppler data stored in the image memory 150 after a diagnosis process, for example. The invoked data serves as display-purpose ultrasound image data after being routed through the image generating circuitry 140. For example, the image memory 150 is realized by using a semiconductor memory element such as a RAM or a flash memory, or a hard disk, an optical disk, or the like.

The storage circuit 160 is configured to store therein control programs for performing the scan (transmitting and receiving ultrasound waves), image processing processes, and display processes, as well as various types of data such as diagnosis information (e.g., patient IDs, medical doctors' observations, etc.), diagnosis protocols, and various types of body marks. Further, the storage circuit 160 may also be used for saving any of the data stored in the image memory 150, as necessary. For example, the storage circuit 160 is realized by using a semiconductor memory element such as a flash memory, or a hard disk, an optical disk, or the like.

The controlling circuitry 170 is configured to control the entirety of the processes performed by the ultrasound diagnosis apparatus 1. More specifically, the controlling circuitry 170 is configured to control processes performed by the transmission and reception circuit 110, the signal processing circuitry 130, and the image generating circuitry 140, on the basis of the various types of setting requests input from the operator via the input device 102 and the various types of control programs and various types of data read from the storage circuit 160. Further, the controlling circuitry 170 is configured to control the display device 103 so as to display ultrasound images based on the display-purpose ultrasound image data stored in the image memory 150. For example, the controlling circuitry 170 is configured to control the display device 103 so as to display a B-mode image based on B-mode image data or a color image based on color image data. Further, the controlling circuitry 170 is configured to control the display device 103 so as to display a color image superimposed on a B-mode image. The controlling circuitry 170 is an example of a display controlling unit or a controlling unit. For example, the controlling circuitry 170 is realized by using a processor. The ultrasound images are examples of images.

Further, the controlling circuitry 170 is configured to control the ultrasound scan by controlling the ultrasound probe 101 via the transmission and reception circuit 110.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). One or more processors are configured to realize the functions by reading the programs saved in the storage circuit 160 and executing the read programs. Alternatively, instead of having the programs saved in the storage circuit 160, it is also acceptable to directly incorporate the programs into the circuits of the one or more processors. In that situation, the one or more processors are configured to realize the functions by reading and executing the programs incorporated in the circuits thereof. Further, the processors according to the present embodiment do not each necessarily have to be structured as a single circuit. It is also acceptable to structure one processor by combining together a plurality of independent circuits, so as to realize the functions thereof. Further, two or more of the circuits (e.g., the signal processing circuitry 130, the image generating circuitry 140, and the controlling circuitry 170) illustrated in FIG. 1 may be integrated in a single processor so as to realize the functions thereof. In other words, the signal processing circuitry 130, the image generating circuitry 140, and the controlling circuitry 170 may be integrated into one piece of processing circuitry realized with the processor.

Figure 12A:
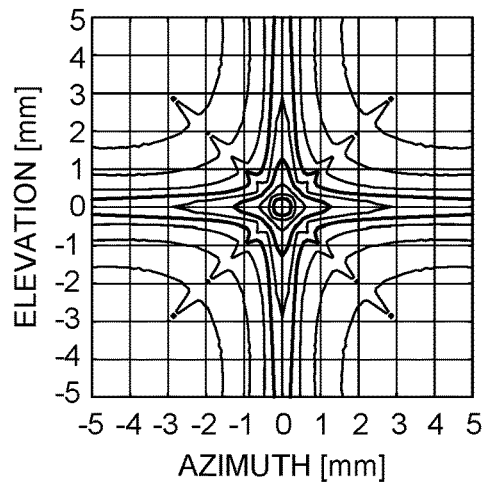
FIG. 12A is a contour line chart at 6-dB intervals expressing a PSF of a first transducer element group having an RCA structure, as viewed from a z-axis direction.
Figure 12B:
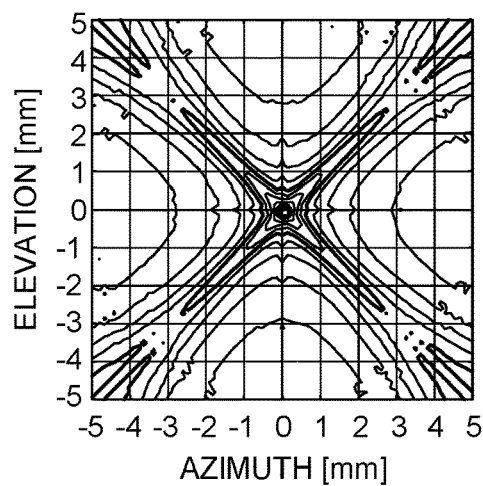
FIG. 12B is a contour line chart at 6-dB intervals expressing a PSF of a second transducer element group having an RCA structure, as viewed from the z-axis direction.
Figure 12C:
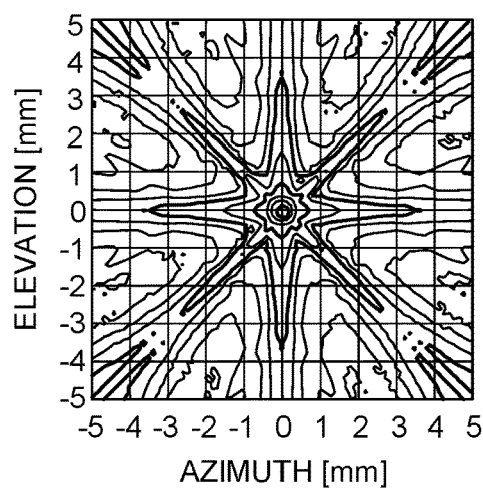
FIG. 12C is a drawing illustrating a result of adding what is depicted in FIG. 12B to what is depicted in FIG. 12A.

FIG. 12A is a contour line chart at 6-dB intervals expressing a PSF of the first transducer element group 106 having the RCA structure, as viewed from the z-axis direction. FIG. 12B is a contour line chart at 6-dB intervals expressing a PSF of the second transducer element group 107 having the RCA structure, as viewed from the z-axis direction. FIG. 12C is a drawing illustrating a result of adding what is depicted in FIG. 12B to what is depicted in FIG. 12A.

Figure 13A:
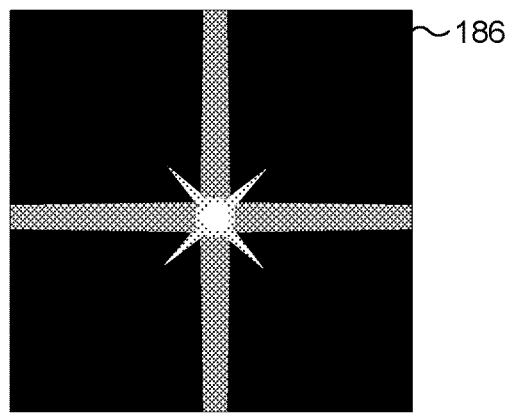
FIG. 13A is a drawing expressing the situation in FIG. 12A by using an image depicting the range from the peak to −40 dB.
Figure 13B:
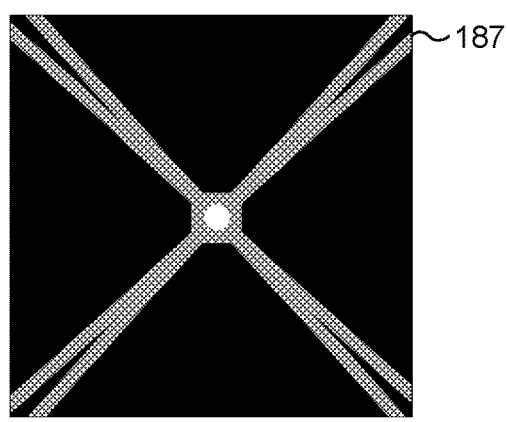
FIG. 13B is a drawing expressing the situation in FIG. 12B by using an image depicting the range from the peak to −40 dB.
Figure 13C:
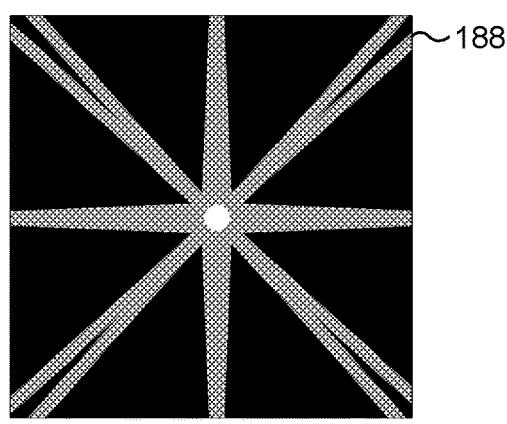
FIG. 13C is a drawing expressing the situation in FIG. 12C by using an image depicting the range from the peak to −40 dB.

FIG. 13A is a drawing expressing the situation in FIG. 12A by using an image 186 depicting the range from the peak to −40 dB. FIG. 13B is a drawing expressing the situation in FIG. 12B by using an image 187 depicting the range from the peak to −40 dB. FIG. 13C is a drawing expressing the situation in FIG. 12C by using an image 188 depicting the range from the peak to −40 dB.

Figure 5A:
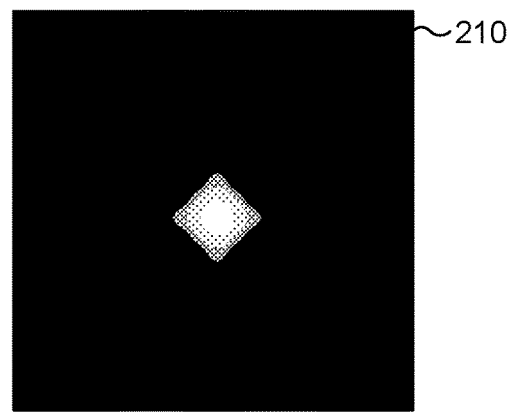
FIG. 5A is a drawing expressing the situation in FIG. 4A by using an image depicting the range from the peak to −40 dB.
Figure 5B:
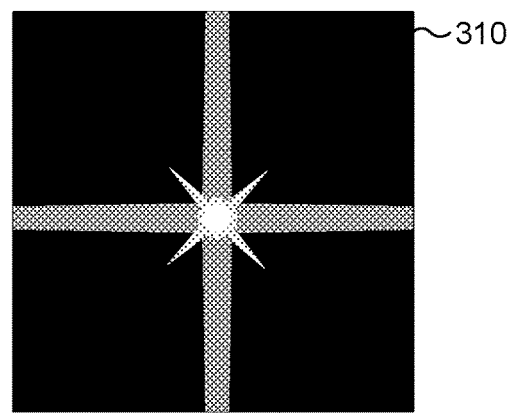
FIG. 5B is a drawing expressing the situation in FIG. 4B by using an image depicting the range from the peak to −40 dB.
Figure 5C:
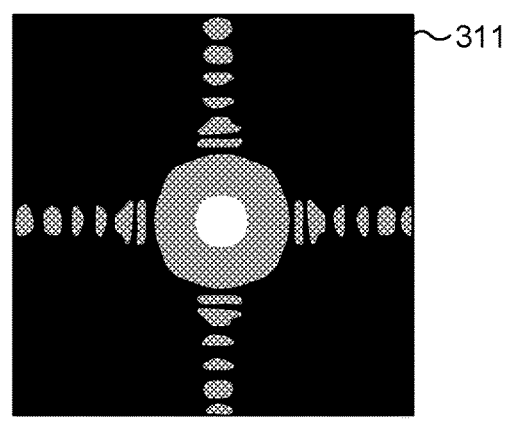
FIG. 5C is a drawing expressing the situation in FIG. 4C by using an image depicting the range from the peak to −40 dB.

As the image 188 in FIG. 13C is compared with the image 310 in FIG. 5B presented earlier, it is observed that, with the ultrasound diagnosis apparatus 1 according to the first embodiment, the side lobes are reduced compared to the example using the ultrasound diagnosis apparatus 300 including the transducer element groups having the RCA structure and not implementing the reception apodization and the transmission apodization.

Further, as the image 188 in FIG. 13C is compared with the image 311 in FIG. 5C presented earlier, it is observed that, with the ultrasound diagnosis apparatus 1 according to the first embodiment, the main lobe is sharper and has higher resolution, compared to the example using the ultrasound diagnosis apparatus 300 including the transducer element groups having the RCA structure and implementing the reception apodization and the transmission apodization.

Figure 14A:
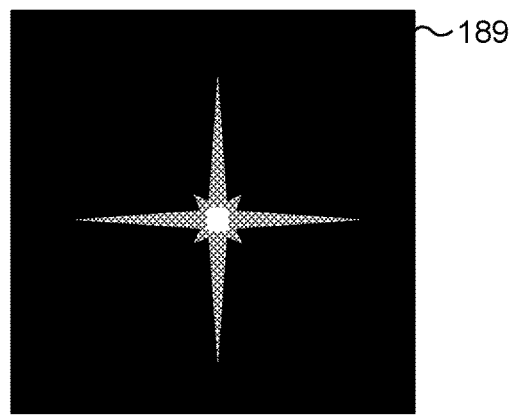
FIG. 14A is a drawing expressing the situation in FIG. 4B presented earlier, by using an image depicting the range from the peak to −30 dB.
Figure 14B:
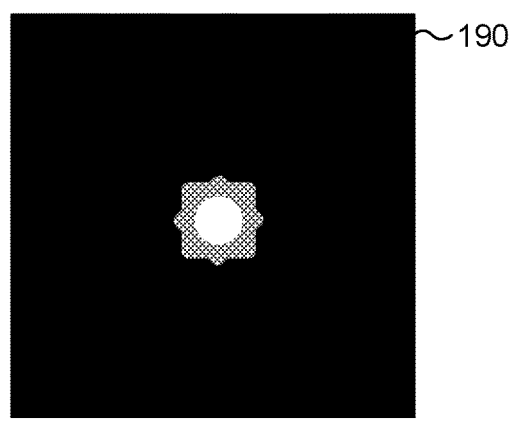
FIG. 14B is a drawing expressing the situation in FIG. 4C presented earlier, by using an image depicting the range from the peak to −30 dB.
Figure 14C:
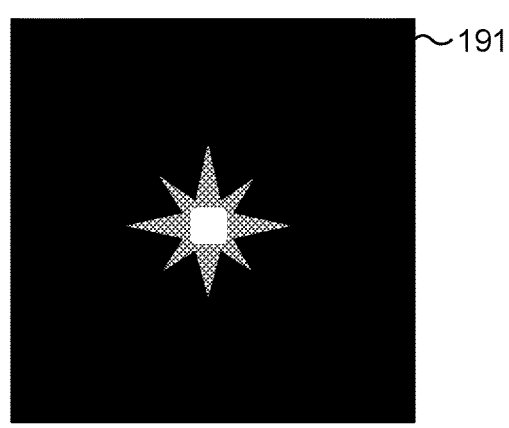
FIG. 14C is a drawing expressing the situation in FIG. 12C presented earlier, by using an image depicting the range from the peak to −30 dB.

Next, to explain advantageous effects of the ultrasound diagnosis apparatus 1 according to the first embodiment in an easy-to-understand manner, images having a display dynamic range at 30 dB are presented in FIGS. 14A to 14C. FIG. 14A is a drawing expressing the situation in FIG. 4B presented earlier, by using an image 189 depicting the range from the peak to −30 dB. FIG. 14B is a drawing expressing the situation in FIG. 4C presented earlier, by using an image 190 depicting the range from the peak to −30 dB. FIG. 14C is a drawing expressing the situation in FIG. 12C presented earlier, by using an image 191 depicting the range from the peak to −30 dB.

As the image 191 in FIG. 14C is compared with the image 189 in FIG. 14A, it is clearly observed that, with the ultrasound diagnosis apparatus 1 according to the first embodiment, the side lobes are reduced compared to the example using the ultrasound diagnosis apparatus 300 including the transducer element groups having the RCA structure and not implementing the reception apodization and the transmission apodization.

Further, as the image 191 in FIG. 14C is compared with the image 190 in FIG. 14B, it is clearly observed that, with the ultrasound diagnosis apparatus 1 according to the first embodiment, the main lobe is sharper and has higher resolution, compared to the example using the ultrasound diagnosis apparatus 300 including the transducer element groups having the RCA structure and implementing the reception apodization and the transmission apodization.

As explained above, it is possible to improve the image quality by using the ultrasound diagnosis apparatus 1 according to the first embodiment.

The ultrasound diagnosis apparatus 1 according to the first embodiment has thus been explained. As explained above, by using the ultrasound diagnosis apparatus 1 according to the first embodiment, it is possible to improve the image quality of the ultrasound images obtained by using the transducer element groups having the RCA structure.

Second Embodiment

In the first embodiment, the example was explained in which the ultrasound probe 101 includes, as the transducer element groups having the RCA structure, the two systems of transducer element groups (the first transducer element group 106 and the second transducer element group 107). However, the ultrasound probe 101 may include three or more systems of transducer element groups, as the transducer element groups having the RCA structure. Thus, this embodiment will be explained as a second embodiment. In the description of the second embodiment, differences from the first embodiment will primarily be explained. Explanations of some of the configurations that are the same as those in the first embodiment may be omitted.

Figure 15A:
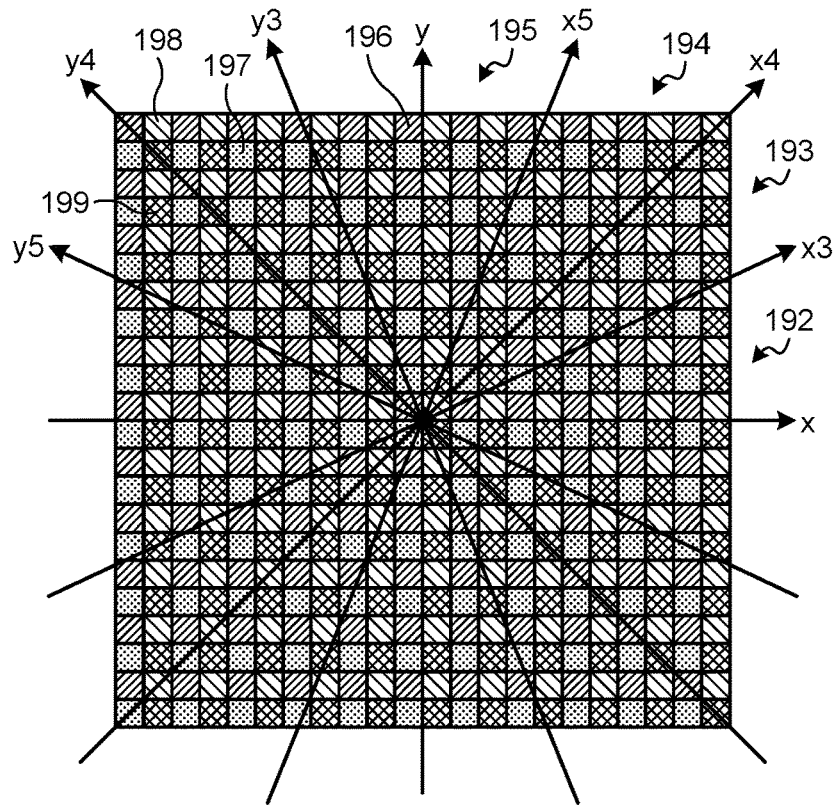
FIG. 15A is a diagram illustrating an exemplary configuration of an ultrasound probe according to a second embodiment.
Figure 15B:
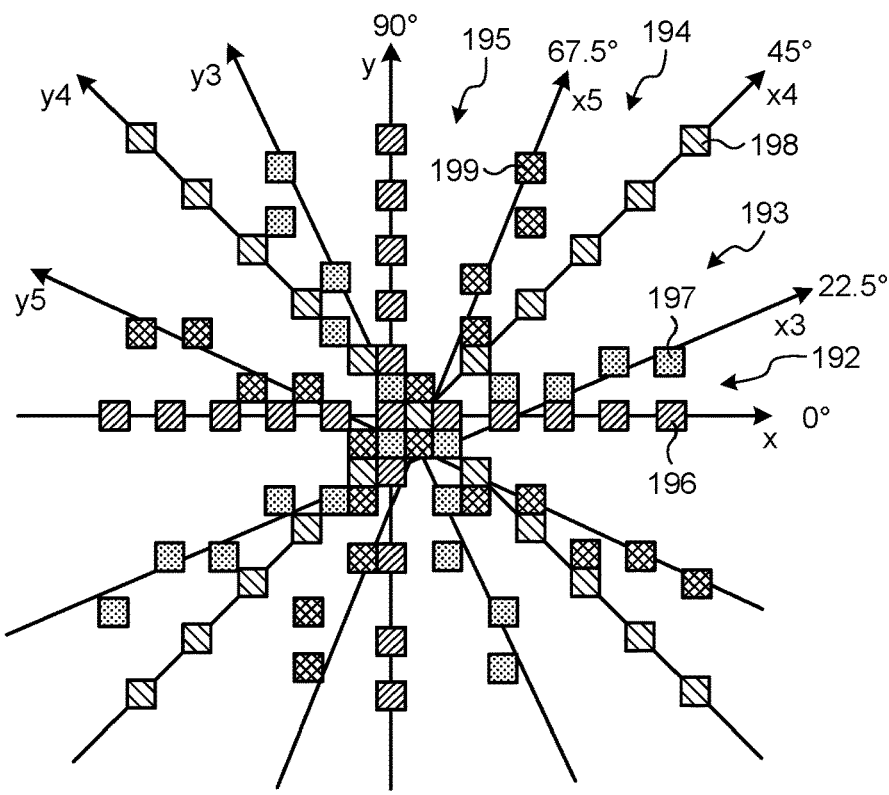
FIG. 15B is another diagram illustrating the exemplary configuration of the ultrasound probe according to the second embodiment.

FIGS. 15A and 15B are diagrams illustrating an exemplary configuration of the ultrasound probe 101 according to the second embodiment. As illustrated in FIG. 15A, the ultrasound probe 101 according to the second embodiment includes a first transducer element group 192 having the RCA structure, a second transducer element group 193 having the RCA structure, a third transducer element group 194 having the RCA structure, and a fourth transducer element group 195 having the RCA structure. In other words, the ultrasound probe 101 includes the four systems of transducer element groups, as transducer element groups having the RCA structure.

In the second embodiment, the ultrasound probe 101 includes a plurality of transducer elements 196, a plurality of transducer elements 197, a plurality of transducer elements 198, and a plurality of transducer elements 199. For example, transducer elements 196, 197, 198, and 199 are assigned as four transducer elements provided in 2×2 blocks arranged in the formation of 2 rows in the x-axis direction by 2 columns in the y-axis direction. Further, a plurality of blocks like this block are arranged two-dimensionally along the x-axis direction and the y-axis direction.

For example, the transducer elements 196, 197, 198, and 199 are configured by using MUTs. Examples of the MUTs include CMUTs. Each of the cells of the MUTs corresponds to one transducer element 196, 197, 198, or 199.

The two-dimensional coordinate system structured with the x-axis and the y-axis illustrated in FIG. 15A corresponds to the first transducer element group 192 having the RCA structure. Further, the two-dimensional coordinate system structured with an x3-axis and a y3-axis illustrated in FIG. 15A corresponds to the second transducer element group 193 having the RCA structure. In this situation, the two-dimensional coordinate system structured with the x3-axis and the y3-axis is a coordinate system obtained by rotating the two-dimensional coordinate system structured with the x-axis and the y-axis by 22.5°, on the origin of the two-dimensional coordinate system structured with the x-axis and the y-axis.

The two-dimensional coordinate system structured with an x4-axis and a y4-axis illustrated in FIG. 15A corresponds to the third transducer element group 194 having the RCA structure. In this situation, the two-dimensional coordinate system structured with the x4-axis and the y4-axis is a coordinate system obtained by rotating the two-dimensional coordinate system structured with the x-axis and the y-axis by 45°, on the origin of the two-dimensional coordinate system structured with the x-axis and the y-axis.

The two-dimensional coordinate system structured with an x5-axis and a y5-axis illustrated in FIG. 15A corresponds to the fourth transducer element group 195 having the RCA structure. In this situation, the two-dimensional coordinate system structured with the x5-axis and the y5-axis is a coordinate system obtained by rotating the two-dimensional coordinate system structured with the x-axis and the y-axis by 67.5°, on the origin of the two-dimensional coordinate system structured with the x-axis and the y-axis.

When the first transducer element group 192 having the RCA structure is to perform ultrasound transmission, as illustrated in FIG. 15B, in the ultrasound probe 101, one of the two surfaces (e.g., the front surface) of each of the plurality of transducer elements 196 arranged in the column direction (the y-axis direction) are connected in common to one another. In other words, in the ultrasound probe 101, the plurality of transducer elements 196 arranged in the column direction (the y-axis direction) are connected in common to one another. As a result, while each of the transducer element groups includes the plurality of transducer elements 196 that are connected in series and arranged in the column direction, the plurality of transducer element groups are arranged in the row direction (the x-axis direction). In this situation, the plurality of transducer elements 196 arranged in the column direction (the y-axis direction) serve as an example of the plurality of first transducer elements.

Further, when the first transducer element group 192 having the RCA structure is to perform ultrasound (reflected wave) reception, as illustrated in FIG. 15B, in the ultrasound probe 101, the other (e.g., the rear surface) of the two surfaces of each of the plurality of transducer elements 196 arranged in the row direction (the x-axis direction) are connected in common to one another. In other words, in the ultrasound probe 101, the plurality of transducer elements 196 arranged in the row direction (the x-axis direction) are connected in common to one another. As a result, while each of the transducer element groups includes the plurality of transducer elements 196 that are connected in series and arranged in the row direction, the plurality of transducer element groups are arranged in the column direction (the y-axis direction). In this situation, the plurality of transducer elements 196 arranged in the row direction (the x-axis direction) serve as an example of the plurality of second transducer elements.

Further, when the second transducer element group 193 having the RCA structure is to perform ultrasound transmission, as illustrated in FIG. 15B, in the ultrasound probe 101, one of the two surfaces (e.g., the front surface) of each of the plurality of transducer elements 197 arranged in the column direction (the y3-axis direction) are connected in common to one another. In other words, in the ultrasound probe 101, the plurality of transducer elements 197 arranged in the column direction (the y3-axis direction) are connected in common to one another. In this situation, the plurality of transducer elements 197 arranged in the column direction (the y3-axis direction) do not denote a plurality of transducer elements 197 arranged in a straight line in the column direction (the y3-axis direction), but denote a plurality of transducer elements 197 included in a range having a certain width in the row direction (the x3-axis direction). As a result, while each of the transducer element groups includes the plurality of transducer elements 197 that are connected in series and arranged in the column direction, the plurality of transducer element groups are arranged in the row direction (the x-axis direction). In this situation, the plurality of transducer elements 197 arranged in the column direction (the y-axis direction) serve as an example of the plurality of first transducer elements.

Further, when the second transducer element group 193 having the RCA structure is to perform ultrasound (reflected wave) reception, as illustrated in FIG. 15B, in the ultrasound probe 101, the other (e.g., the rear surface) of the two surfaces of each of the plurality of transducer elements 197 arranged in the row direction (the x3-axis direction) are connected in common to one another. In other words, in the ultrasound probe 101, the plurality of transducer elements 197 arranged in the row direction (the x3-axis direction) are connected in common to one another. In this situation, the plurality of transducer elements 197 arranged in the row direction (the x3-axis direction) do not denote a plurality of transducer elements 197 arranged in a straight line in the row direction (the x3-axis direction), but denote a plurality of transducer elements 197 included in a range having a certain width in the column direction (the y3-axis direction). As a result, while each of the transducer element groups includes the plurality of transducer elements 197 that are connected in series and arranged in the row direction, the plurality of transducer element groups are arranged in the column direction (the y3-axis direction). In this situation, the plurality of transducer elements 197 arranged in the row direction (the x3-axis direction) serve as an example of the plurality of second transducer elements.

Further, when the third transducer element group 194 having the RCA structure is to perform ultrasound transmission, as illustrated in FIG. 15B, in the ultrasound probe 101, one of the two surfaces (e.g., the front surface) of each of the plurality of transducer elements 198 arranged in the column direction (the y4-axis direction) are connected in common to one another. In other words, in the ultrasound probe 101, the plurality of transducer elements 198 arranged in the column direction (the y4-axis direction) are connected in common to one another. In this situation, the plurality of transducer elements 198 arranged in the column direction (the y4-axis direction) do not denote a plurality of transducer elements 198 arranged in a straight line in the column direction (the y4-axis direction), but denote a plurality of transducer elements 198 included in a range having a certain width in the row direction (the x4-axis direction). As a result, while each of the transducer element groups includes the plurality of transducer elements 198 that are connected in series and arranged in the column direction, the plurality of transducer element groups are arranged in the row direction (the x4-axis direction). In this situation, the plurality of transducer elements 198 arranged in the column direction (the y4-axis direction) serve as an example of the plurality of first transducer elements.

Further, when the third transducer element group 194 having the RCA structure is to perform ultrasound (reflected wave) reception, as illustrated in FIG. 15B, in the ultrasound probe 101, the other (e.g., the rear surface) of the two surfaces of each of the plurality of transducer elements 198 arranged in the row direction (the x4-axis direction) are connected in common to one another. In other words, in the ultrasound probe 101, the plurality of transducer elements 198 arranged in the row direction (the x4-axis direction) are connected in common to one another. In this situation, the plurality of transducer elements 198 arranged in the row direction (the x4-axis direction) do not denote a plurality of transducer elements 198 arranged in a straight line in the row direction (the x4-axis direction), but denote a plurality of transducer elements 198 included in a range having a certain width in the column direction (the y4-axis direction). As a result, while each of the transducer element groups includes the plurality of transducer elements 198 that are connected in series and arranged in the row direction, the plurality of transducer element groups are arranged in the column direction (the y4-axis direction). In this situation, the plurality of transducer elements 198 arranged in the row direction (the x4-axis direction) serve as an example of the plurality of second transducer elements.

Further, when the fourth transducer element group 195 having the RCA structure is to perform ultrasound transmission, as illustrated in FIG. 15B, in the ultrasound probe 101, one of the two surfaces (e.g., the front surface) of each of the plurality of transducer elements 199 arranged in the column direction (the y5-axis direction) are connected in common to one another. In other words, in the ultrasound probe 101, the plurality of transducer elements 199 arranged in the column direction (the y5-axis direction) are connected in common to one another. In this situation, the plurality of transducer elements 199 arranged in the column direction (the y5-axis direction) do not denote a plurality of transducer elements 199 arranged in a straight line in the column direction (the y5-axis direction), but denote a plurality of transducer elements 199 included in a range having a certain width in the row direction (the x5-axis direction). As a result, while each of the transducer element groups includes the plurality of transducer elements 199 that are connected in series and arranged in the column direction, the plurality of transducer element groups are arranged in the row direction (the x5-axis direction). In this situation, the plurality of transducer elements 199 arranged in the column direction (the y5-axis direction) serve as an example of the plurality of first transducer elements.

Further, when the fourth transducer element group 195 having the RCA structure is to perform ultrasound (reflected wave) reception, as illustrated in FIG. 15B, in the ultrasound probe 101, the other (e.g., the rear surface) of the two surfaces of each of the plurality of transducer elements 199 arranged in the row direction (the x5-axis direction) are connected in common to one another. In other words, in the ultrasound probe 101, the plurality of transducer elements 199 arranged in the row direction (the x5-axis direction) are connected in common to one another. In this situation, the plurality of transducer elements 199 arranged in the row direction (the x5-axis direction) do not denote a plurality of transducer elements 199 arranged in a straight line in the row direction (the x5-axis direction), but denote a plurality of transducer elements 199 included in a range having a certain width in the column direction (the y5-axis direction). As a result, while each of the transducer element groups includes the plurality of transducer elements 199 that are connected in series and arranged in the row direction, the plurality of transducer element groups are arranged in the column direction (the y5-axis direction). In this situation, the plurality of transducer elements 199 arranged in the row direction (the x5-axis direction) serve as an example of the plurality of second transducer elements.

Further, by using the four systems of transducer element groups (the first transducer element group 192, the second transducer element group 193, the third transducer element group 194, and the fourth transducer element group 195) described above, the ultrasound diagnosis apparatus 1 according to the second embodiment is configured to perform processes similar to those performed by the ultrasound diagnosis apparatus 1 according to the first embodiment while using the two systems of transducer element groups (the first transducer element group 106 and the second transducer element group 107).

As explained above, the ultrasound probe 101 according to the second embodiment includes the plurality of transducer elements 196, 197, 198, and 199 arranged two-dimensionally. Further, the ultrasound probe 101 includes the plurality of transducer element groups (the first transducer element group 192, the second transducer element group 193, the third transducer element group 194, and the fourth transducer element group 195) of the Row-Column Addressing type in which, when the ultrasound transmission is to be performed, the plurality of transducer elements 196, the plurality of transducer elements 197, the plurality of transducer elements 198, or the plurality of transducer elements 199 that are arranged in the direction (e.g., the column direction in the above example) of one of the two axes (e.g., the x- and y-axes, the x3- and y3-axes, the x4- and y4-axes, or the x5- and y5-axes) intersecting each other are connected in common to one another and in which when the ultrasound reception is to be performed, the plurality of transducer elements 196, the plurality of transducer elements 197, the plurality of transducer elements 198, or the plurality of transducer elements 199 that are arranged in the direction (e.g., the row direction in the above example) of the other of the two axes are connected in common to one another.

Further, in the second embodiment, the plurality of sets each made up of two axes (e.g., the set made up of the x- and y-axes, the set made up of the x3- and y3-axes, the set made up of the x4- and y4-axes, and the set made up of the x5- and y5-axes) corresponding to the plurality of transducer element groups (the first transducer element group 192, the second transducer element group 193, the third transducer element group 194, and the fourth transducer element group 195) of the Row-Column Addressing type are mutually different.

Further, in the second embodiment, the ultrasound probe 101 includes the plurality of transducer element groups (the first transducer element group 192, the second transducer element group 193, the third transducer element group 194, and the fourth transducer element group 195) of the Row-Column Addressing type configured so that the product of the angular interval (e.g., 22.5°) between the plurality of sets each made up of two axes (e.g., the set made up of the x- and y-axes, the set made up of the x3- and y3-axes, the set made up of the x4- and y4-axes, and the set made up of the x5- and y5-axes) corresponding to the plurality of transducer element groups (the first transducer element group 192, the second transducer element group 193, the third transducer element group 194, and the fourth transducer element group 195) of the Row-Column Addressing type and the quantity of the plurality of transducer element groups (e.g., 4) of the Row-Column Addressing type is 90°.

The ultrasound diagnosis apparatus 1 according to the second embodiment has thus been explained. The ultrasound diagnosis apparatus 1 according to the second embodiment achieves advantageous effects similar to those achieved by the ultrasound diagnosis apparatus 1 according to the first embodiment.

Further, the programs executed by the processors are provided as being incorporated, in advance, into a Read-Only Memory (ROM), a storage circuit, or the like. Alternatively, the programs may be provided as being recorded on a non-transitory computer-readable storage medium such as a Compact Disk Read-Only Memory (CD-ROM), a flexible disk (FD), a Compact Disk Recordable (CD-R), a Digital Versatile Disk (DVD), or the like, in a file that is in an installable or executable format for those devices. Further, the programs may be stored in a computer connected to a network such as the Internet, so as to be provided or distributed as being downloaded via the network. For example, the programs are structured with modules including the processing functions described above. In the actual hardware, as a result of a CPU reading and executing the programs from a storage medium such as a ROM, the modules are loaded into a main storage device so as to be generated in the main storage device.

According to at least one aspect of the embodiments described above, it is possible to improve the image quality of the ultrasound images obtained by using the transducer element groups having the RCA structure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
an ultrasound probe including a plurality of transducer elements arranged two-dimensionally and including a plurality of transducer element groups of a Row-Column Addressing type in which, when ultrasound transmission is to be performed, a plurality of first transducer elements arranged in a direction of one of two axes intersecting each other are connected in common to one another and in which, when ultrasound reception is to be performed, a plurality of second transducer elements arranged in a direction of the other of the two axes are connected in common to one another; and
processing circuitry configured to perform a beam forming process on a plurality of reception signals output from the plurality of transducer element groups, to generate ultrasound image data on a basis of a signal obtained from the beam forming processes, and to cause a display device to display an ultrasound image based on the ultrasound image data, wherein
each of the plurality of transducer element groups outputs, as each of the plurality of reception signals, a reception signal obtained by adding up signals output from the plurality of second transducer elements connected in common to one another,
a plurality of sets that are each made up of the two axes and correspond to the plurality of transducer element groups of the Row-Column Addressing type are mutually different,
with respect to the plurality of the transducer element groups, a direction in which a plurality of first transducer elements in one of the plurality of the transducer element groups connected in common to one another is arranged and a direction in which a plurality of first transducer elements in another of the plurality of the transducer element groups connected in common to one another is arranged are mutually different, and
a direction in which a plurality of second transducer elements in one of the plurality of the transducer element groups connected in common to one another arranged and a direction in which a plurality of second transducer elements in other of the plurality of the transducer element groups connected in common to one another arranged are mutually different.

2. The ultrasound diagnosis apparatus according to claim 1, wherein the processing circuitry is configured to add up two or more of the signals generated with respect to the plurality of the transducer element groups and obtained from two or more of the beam forming processes and is configured to generate the ultrasound image data on the basis of a signal resulting from the addition.

3. The ultrasound diagnosis apparatus according to claim 1, wherein, with respect to each of the plurality of transducer element groups, the processing circuitry is configured to perform the beam forming process on the plurality of reception signals output from the plurality of second transducer elements, without implementing apodization.

4. The ultrasound diagnosis apparatus according to claim 1, wherein the ultrasound probe includes the plurality of transducer element groups of the Row-Column Addressing type configured so that a product of an angular interval between the plurality of sets corresponding to the plurality of transducer element groups of the Row-Column Addressing type and a quantity of the plurality of transducer element groups of the Row-Column Addressing type is 90.

5. The ultrasound diagnosis apparatus according to claim 1, wherein the ultrasound probe includes the plurality of transducer elements configured by using Micromachined Ultrasonic Transducers (MUTs).

6. The ultrasound diagnosis apparatus according to claim 1, wherein each of the plurality of transducer element groups includes a plurality of first transducer element groups arranged in a direction of one of two axes corresponding to each of the plurality of transducer element groups and a plurality of second transducer element groups arranged in a direction of the other of the two axes corresponding to each of the plurality of transducer element groups.

7. The ultrasound diagnosis apparatus according to claim 6, wherein each of the plurality of transducer element groups transmit an ultrasound wave, to which a transmission delay is applied, in the direction of the other of the two axes.

8. The ultrasound diagnosis apparatus according to claim 1, wherein the plurality of sets corresponding to the plurality of transducer element groups are arranged at different angles from each other.

9. The ultrasound diagnosis apparatus according to claim 1, wherein the direction in which the plurality of first transducer elements in one of the plurality of the transducer element groups connected in common to one another arranged is different from the direction in which the plurality of first transducer elements in other of the plurality of the transducer element groups connected in common to one another arranged by a 45-degree angle, and
the direction in which the plurality of second transducer elements in one of the plurality of the transducer element groups connected in common to one another arranged is different from the direction in which the plurality of second transducer elements in other of the plurality of the transducer element groups connected in common to one another arranged by the 45-degree angle.

10. The ultrasound diagnosis apparatus according to claim 1, wherein, when ultrasound transmission is to be performed, ultrasound waves having transmission delay period in correspondence with each of the plurality of the transducer element groups are converged so as to propagate in a predetermined direction.

\* \* \* \* \*